(12) United States Patent  (10) Patent No.: US 8,852,122 B2
Mao et al.  (45) Date of Patent: Oct. 7, 2014

(54) LIQUID SAMPLING, STORAGE, TRANSFER AND DELIVERY DEVICE

(71) Applicant: Porex Corporation, Fairburn, GA (US)

(72) Inventors: Guoqiang Mao, Peachtree City, GA (US); James P. Wingo, Peachtree City, GA (US)

(73) Assignee: Porex Corporation, Fairburn, GA (US)

( * ) Notice: Subject to any disclaimer, the term of this patent is extended or adjusted under 35 U.S.C. 154(b) by 0 days.

(21) Appl. No.: 14/254,325

(22) Filed: Apr. 16, 2014

(65) Prior Publication Data

US 2014/0249451 A1  Sep. 4, 2014

Related U.S. Application Data

(63) Continuation of application No. 14/007,496, filed as application No. PCT/US2012/034046 on Apr. 18, 2012.

(60) Provisional application No. 61/476,834, filed on Apr. 19, 2011.

(51) Int. Cl.
*A61B 5/00* (2006.01)

(52) U.S. Cl.
USPC .......................................... 600/572; 600/563

(58) Field of Classification Search
USPC ................................................ 600/572, 583
See application file for complete search history.

(56) References Cited

U.S. PATENT DOCUMENTS

| | | | |
|---|---|---|---|
| 3,164,279 A | 1/1965 | Towns | |
| 4,580,918 A | 4/1986 | Baker et al. | |
| 4,635,488 A * | 1/1987 | Kremer | 73/864.72 |
| 4,678,757 A | 7/1987 | Rapkin | |
| 4,720,017 A * | 1/1988 | Pestes | 215/227 |
| 5,238,649 A | 8/1993 | Nason | |
| 5,362,654 A | 11/1994 | Pouletty | |
| 5,480,250 A | 1/1996 | Birden | |
| 5,523,055 A * | 6/1996 | Hansen et al. | 422/401 |
| 5,607,766 A | 3/1997 | Berger | |
| 6,171,260 B1 * | 1/2001 | Hochmeister et al. | 600/572 |
| 6,180,395 B1 * | 1/2001 | Skiffington et al. | 435/287.6 |
| 6,303,081 B1 | 10/2001 | Mink et al. | |
| 7,819,822 B2 * | 10/2010 | Calasso et al. | 600/583 |
| 7,999,221 B2 * | 8/2011 | Plows et al. | 250/282 |

(Continued)

FOREIGN PATENT DOCUMENTS

| | | |
|---|---|---|
| EP | 0940678 | 9/1999 |
| JP | 61237059 | 10/1986 |

(Continued)

OTHER PUBLICATIONS

U.S. Appl. No. 14/007,496, Non-Final Office Action mailed on May 21, 2014, 10 pages.

(Continued)

*Primary Examiner* — Max Hindenburg

(74) *Attorney, Agent, or Firm* — Kilpatrick Townsend & Stockton LLP

(57) ABSTRACT

The present invention provides a liquid sampling, storage, transfer and delivery device comprising housing containing a porous nib. The porous nib in the device contacts the sample, collects the sample, stores the sample, transports the sample inside its porous matrix and releases the sample from the porous matrix upon demand.

25 Claims, 12 Drawing Sheets

(56) References Cited

U.S. PATENT DOCUMENTS

| | | | |
|---|---|---|---|
| 8,141,717 B2* | 3/2012 | Wingo et al. | 210/510.1 |
| 8,623,198 B2* | 1/2014 | Chatelier et al. | 205/792 |
| 2002/0193030 A1 | 12/2002 | Yao et al. | |
| 2005/0252820 A1 | 11/2005 | Sanchez-Felix et al. | |
| 2007/0202009 A1 | 8/2007 | Nunes et al. | |
| 2008/0199363 A1 | 8/2008 | Mao | |
| 2011/0004122 A1* | 1/2011 | Sangha | 600/572 |
| 2014/0018701 A1 | 1/2014 | Mao et al. | |

FOREIGN PATENT DOCUMENTS

| | | |
|---|---|---|
| JP | 63141227 | 6/1988 |
| JP | 63215939 | 9/1988 |
| JP | 05503230 | 6/1993 |
| JP | 05187976 | 7/1993 |
| JP | 09190796 | 7/1997 |
| JP | 11076213 | 3/1999 |
| JP | 2005017280 | 1/2005 |
| JP | 2005055316 | 3/2005 |
| JP | 2005283366 | 10/2005 |
| JP | 2008521019 | 6/2008 |
| WO | 9502996 | 2/1995 |
| WO | 2008122908 | 10/2008 |
| WO | 2010127059 | 11/2010 |
| WO | 2012145379 | 10/2012 |

OTHER PUBLICATIONS

PCT/US2012/034046, "International Preliminary Report on Patentability", Oct. 31, 2013, 8 pages.

PCT/US2012/034046, "International Search Report and Written Opinion", Jun. 28, 2012, 12.

Japanese Patent Application No. 2014-506506, Office Action mailed Jun. 24, 2014, 9 pages.

* cited by examiner

Nib examples

Nib examples: with tip and stem

Example of breaking nib tip into a container

Nip tip released after pushing against the container wall

Example of press active retractable release

The sample nib can be retracted into housing after sampling

Release sample nib

Sample nib can be capped

LIQUID SAMPLING, STORAGE, TRANSFER AND DELIVERY DEVICE

CROSS REFERENCE TO RELATED APPLICATIONS

This application is a Continuation of U.S. Ser. No. 14/007,496 titled "Liquid Sampling, Storage, Transfer and Delivery Device," filed Sep. 25, 2013, which application is a U.S. national phase patent application under 35 U.S.C. 371 of International Patent Application No. PCT/US2012/034046 entitled "Liquid Sampling, Storage, Transfer and Delivery Device" filed Apr. 18, 2012, which claims benefit of priority of U.S. Patent Application No. 61/476,834 filed on Apr. 19, 2011. These applications are incorporated herein by reference in their entireties.

FIELD OF THE INVENTION

The present invention provides devices useful in liquid sampling, storage, transfer and delivery. The devices comprise a housing containing a sintered porous matrix in the form of a porous nib which can absorb the liquid sample for storage, transfer and delivery.

BACKGROUND OF THE INVENTION

Liquid samples are analyzed for many different substances contained within the samples in a wide variety of industries. Such industries include but are not limited to biomedical research, clinical chemistry, environmental analysis, forensics, toxicology, pharmacology, petrochemicals, etc. Most laboratories employ devices for handing liquid samples. There is a need for devices that are capable of efficiently absorbing a liquid sample. Such absorbed samples may be analyzed soon after collection or may be transferred for subsequent analysis at a convenient time or location. There is a need for such devices to be capable of storing a sample until the time for analysis, when the device must release the sample.

Most current sampling devices require a large amount of a sample, such as blood drawing tubes. With the recent development of mass spectrometry, the detection sensitivity has been improved and amount of sample needed for detection is significantly reduced. In some situations, it is difficult to obtain a large amount of blood, such as from a small experimental animal, a newborn or elderly individuals with vascular problems. What is needed are liquid sampling devices that can collect relatively small amounts of a sample (less than 1 ml) and preserve the sample for a prolonged period.

Yet another drawback for most common sampling devices is that they require low temperature preservation. If a device can preserve the sample in an ambient temperature, it will reduce the cost and the chance for sample degradation. Whatman dry blood cards have been used in sample collection. However, the dry blood cards are open systems, the sample may be contaminated during sample storage, or sample transport process by the package materials, adsorption and human error. The dry blood cards also need to have a separate puncture device, a liquid transfer device and a cutting device to collect sample and release the sample. Multiple steps increase the chances of human error and contamination. Accordingly, there is a need for sample collection devices that can puncture the target, collect a small amount of a liquid sample, preserve the sample, treat the sample and release the sample to the downstream analytical devices in a closed system.

SUMMARY

The present invention solves these problems and provides a liquid sampling, storage, transfer and delivery device comprising a porous component. The porous component comprises a sintered porous matrix made by fusing individual particles together in a sintering process to form the matrix. The porous component in the device contacts the sample, collects the sample, stores the sample, transports the sample inside its porous matrix and releases the sample from the porous matrix upon demand. The sample originally is in liquid form when contacted by the porous component; however, the sample can be in either a liquid form or in a dry form once inside the porous component. In one embodiment, the liquid sample is a biological fluid. In a specific embodiment, the biological fluid is blood.

The porous components of the devices comprise porous nibs which are employed in operation of the device. These devices are employed for sample collection, storage, transport and/or delivery. In one embodiment, samples are delivered to an analytical device. In another embodiment, these porous nibs may be used to apply a solution or a sample to a surface. In one embodiment, these porous nibs are sintered porous nibs.

The porous component in the device can be porous plastics, porous metals, porous ceramics, and fibers or extruded plastic or metal with internal channels. In a specific embodiment, the porous plastic is a sintered porous plastic. In one embodiment, the porous component is in the form of a nib. In another embodiment, the nib comprises a nib tip and a nib stem connected to the nib tip. In one embodiment, the porous plastic nibs are removably attached to the stem. Such removable attachment facilitates separation of the nib tip from the stem. For example, the nib tip may be pressed against a surface with sufficient force to separate the nib tip from the stem. In a specific embodiment, the nib has a sharp point. The nib can be molded or ground into a desired shape.

These porous nibs may comprise functional additives that are useful in preserving an analyte of interest, for example, by lysing cells, by inactivating enzymes that may degrade the analyte, by chelating ions, or by preserving nucleic acids. Functional additives include, but not limited to the following: polyelectrolytes, C-18, C-8 or C-4 modified silica, silica gel, ion exchange material, controlled porous glass (CPG), solid phase extraction (SPE) media, cell lysis reagents, protein denaturing additives, chemicals that denature or de-activate proteins and/or lyse cells, anti-oxidants, chemicals that preserve the analyte to be measured in the sample, enzyme inhibitors, antimicrobials, and color change indicators, chelating agents, surfactants, DNA stabilizing agents, a weak acid, such as Tris(hydroxymethyl)aminomethane (TRIS), a chaotropic agent, an anti-coagulant, or a combination thereof.

Porous nibs may also be surface activated by treating with plasma, for example, oxygen plasma. Such treatment may increase hydrophilicity of the porous nibs.

Porous nibs may be treated with polyelectrolyte solutions to increase hydrophilicity.

In one embodiment, the device is in a writing instrument format. In a specific embodiment, the device is in a pen format. The porous nib is located at the tip of the device near the opening of the device. A device may contain a plurality of nibs. In one embodiment, the porous component is hydrophilic and liquid can wick into the porous component through capillary force. In one embodiment, the device can be used to apply a solution or a sample to a surface. In another embodiment, the device can purify the sample inside its porous component. In another embodiment, the device can release the sample to a detection device or to a suitable receptacle for storage, transport or analysis. The device may be capped to protect the nibs and prevent contamination of clean nibs or nibs containing a sample.

DETAILED DESCRIPTION

The present invention provides a liquid sampling, storage, transfer and delivery device comprising a porous component. The porous component in the device contacts the sample, collects the sample, stores the sample, transports the sample inside its porous matrix and releases the sample from the porous matrix upon demand. The sample originally is in liquid form when contacted by the porous component; however, the sample can be in either a liquid form or in a dry form once inside the porous component. In one embodiment, the liquid sample is a biological fluid. In a specific embodiment, the biological fluid is blood.

The porous components of the devices comprise porous nibs which are employed in operation of the device. These devices are employed for sample collection, storage, transport and/or delivery. In one embodiment, samples are delivered to an analytical device. In another embodiment, these porous nibs may be used to apply a solution or a sample to a surface. In one embodiment, these porous nibs are sintered porous nibs.

The porous component in the device can be porous plastics, porous metals, porous ceramics, and fibers or extruded plastic or metal with internal channels. In a specific embodiment, the porous plastic is a sintered porous plastic. In one embodiment, the porous component is in the form of a nib. In another embodiment, the nib comprises a nib tip and a nib stem connected to the nib tip. In one embodiment, the porous plastic nibs are removably attached to the stem. Such removable attachment facilitates separation of the nib tip from the stem. For example, the nib tip may be pressed against a surface with sufficient force to separate the nib tip from the stem. In a specific embodiment, the nib has a sharp point. The nib can be molded or ground into a desired shape.

In one embodiment, the device is in a writing instrument format. In a specific embodiment, the device is in a pen format. The porous nib is located at the tip of the device. A device may contain a plurality of nibs. In one embodiment, the porous component is hydrophilic and liquid can wick into the porous component through capillary force. In one embodiment, the device can be used to apply a solution or a sample to a surface. In another embodiment, the device can purify the sample inside its porous component. In another embodiment, the device can release the sample to a detection device or to a suitable receptacle for storage, transport or analysis. The device may be capped to protect the nibs and prevent contamination of clean nibs or nibs containing a sample.

The term animal includes but is not limited to mammals and humans in this application.

Nibs

Figure 1:
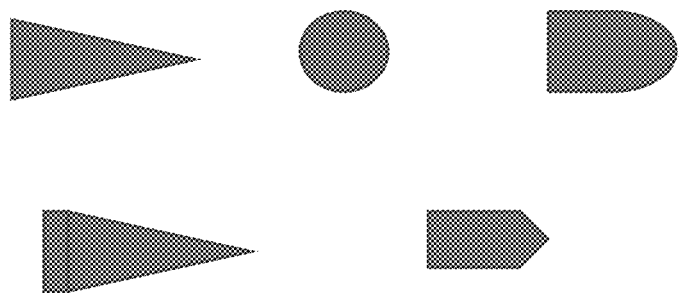
FIG. 1. Schematic representation of various shapes of nibs without breakable tips and stems.
Figure 2:
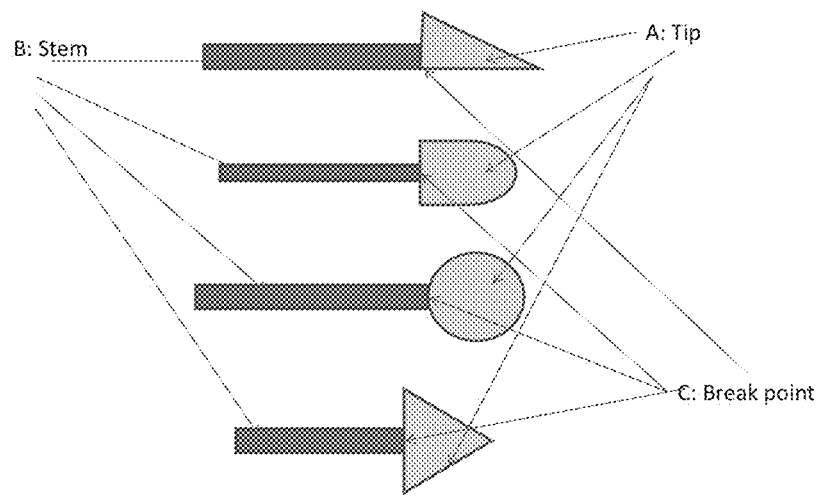
FIG. 2. Schematic representation of various shapes of with tips, stems and break points for separation of the tip and stem.
Figure 3:
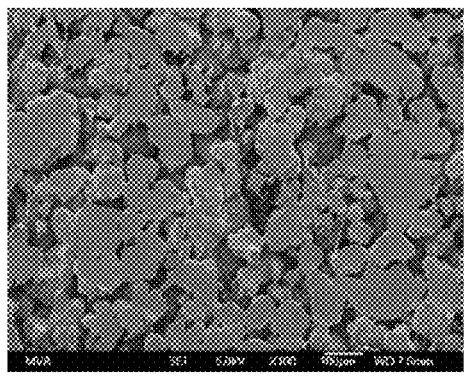
FIG. 3. Scanning electron micrographs of sintered porous plastic nibs (cross-section (left panel) and surface (right panel)).
Figure 3:
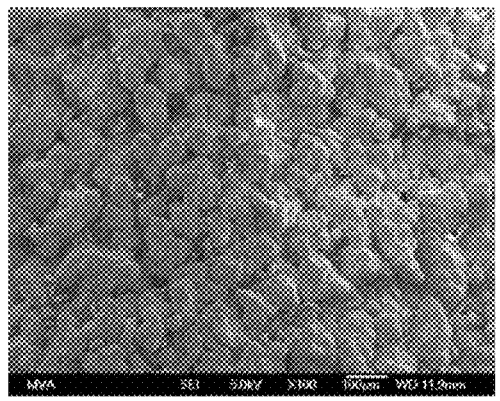
Figure 4:
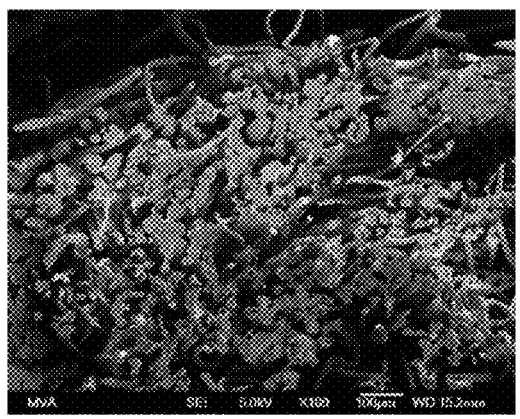
FIG. 4. Scanning electron micrographs of fiber nibs (cross-section (left panel) and surface (right panel)).
Figure 4:
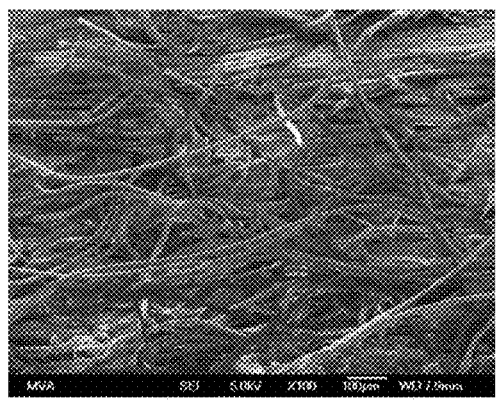
Figure 5:
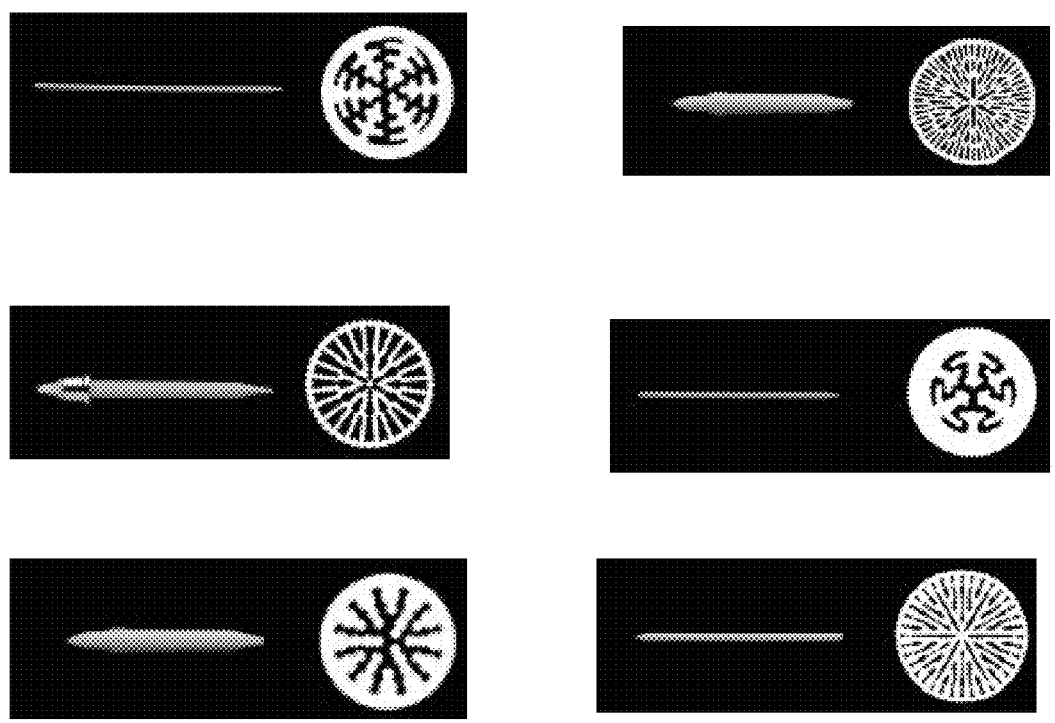
FIG. 5. Schematic representations of extruded plastic nibs with internal channel structure.

The nibs for use in the embodiments described herein may be made from a number of types of materials and may have a number of various shapes. For example, they may be polymeric, plastic, natural polymers, metal, ceramic, glass, or fiber nibs, examples of which are described further below. The materials may be sintered in order to create a porous structure that can absorb, retain and/or store a sample material. Regardless of the type of material used, the nibs may also have functional additives incorporated therein. Such additives may enhance immobilization of a target molecule. It is possible for the nibs to be designed for insertion directly into the device. Examples of such nibs are shown in FIG. 1. It is also possible for the nibs to be used in connection with a nib stem, such that the nib forms a nib tip and the stem forms a nib stem. Examples of such nibs are shown in FIG. 2.

In general, the nib shapes may be any appropriate shape that allows the nib to perform the desired functions described herein. For example, the nib may provided as a sharp point; a rounded or spherical shape; an oval shape; an angular shape such as a triangular shape, pyramidal shape, or an angled tip; a square shape, a bullet head shape, a chisel shape, a marker-tip-like shape, a needle shape, a rod shape, an elongated element, a short element, or any other appropriate shape that will allow the nib to achieve the functions described herein. The nibs can also be provided as a fine tube form that can collect a sample through capillary force. In fact, in any of the described shapes, the nibs may define a hollow internal tube or other channel-like portion, which can help encourage capillary action. Alternatively, the nib may be formed entirely of the desired material without a hollow internal tube or channel. There may be only one nib provided, or more than one nib may be used, having the same or different shapes and configurations.

Composition and Properties of Nibs
  Polymeric Nibs:
  Polymeric nibs can be made in different ways and with different materials. Polymeric nibs include:
    Plastic Nibs.

The plastic nibs may be made from a variety of plastics such as polyethylene. Polyethylenes which may be employed include but are not limited to high density polyethylene (HDPE), low density polyethylene (LDPE) and ultra high molecular weight polyethylene (UHMWPE). Nibs may also be made from polypropylene (PP), polyvinylidene fluoride (PVDF), polyamides, polyacrylates, polystyrene, polyacrylic nitrile (PAN), ethylene-vinyl acetate (EVA), polyesters, polycarbonates, or polytetrafluoroethylene (PTFE). Plastic nibs may also be made from more than one of the aforementioned plastics. In one embodiment, a plastic nib is made from about 30% PP and about 70% PE (wt:wt %). In other embodiments when PP and PE are combined, PP may be present in a range of from about 100% to about 0% and PE may be present in a range of from about 0 to about 100% (100% to 0%:0% to 100% wt:wt %). When PE is combined with other polymers, the PE is present in at least about 50% (wt %).

In one embodiment the plastic is HDPE. In other embodiments the plastic is UHMWPE, PP, polyamides, or polyacrylic nitrile.

Plastic nibs can also contain other additive materials, such as carbon, silica, control porous glass (CPG), ion exchange resins, modified silica, such as C-8 and C-18, or clays for improved binding and purification properties of the nibs.

In one specific embodiment, plastic nibs are sintered porous plastic nibs.

Plastic Nibs Containing Elastomers

In another embodiment, the plastic porous nibs can also comprise elastomeric particles. Elastomeric particles include but are not limited to ethylene-styrene-butadiene-ethylene copolymer, polyethylene-polypropylene copolymer, natural rubbers, polyacrylonitrile, and vulcanized rubbers.

In addition to at least one plastic, sintered plastic polymeric nibs of the present invention can comprise at least one elastomer. In some embodiments, sintered plastic polymeric nibs of the present invention comprise a plurality of elastomers. Elastomers suitable for use in sintered plastic polymeric nibs of the present invention, according to some embodiments, comprise thermoplastic elastomers (TPE). Themoplastic elastomers are elastomers that have melting points and do not have a chemically crosslinked structure. Thermoplastic elastomers, in some embodiments, comprise polyurethanes and thermoplastic polyurethanes (TPU). Thermoplastic polyurethanes, in some embodiments, include multiblock copolymers comprising a polyurethane and a polyester or polyether.

In other embodiments, elastomers suitable for use in sintered plastic polymeric nibs of the present invention comprise polyisobutylene, polybutenes, butyl rubber, or combinations thereof. In another embodiment, elastomers comprise copolymers of ethylene and other polymers such as polyethylene-propylene copolymer, referred to as EPM, ethylene-butene copolymer, polyethylene-octene copolymer, and polyethylene-hexene copolymer. In a further embodiment, elastomers comprise chlorinated polyethylene or chloro-sulfonated polyethylene.

In some embodiments, elastomers suitable for use in sintered plastic polymeric nibs of the present invention comprise 1,3-dienes and derivatives thereof. 1,3-dienes include styrene-1,3-butadiene (SBR), styrene-1,3-butadiene terpolymer with an unsaturated carboxylic acid (carboxylated SBR), acrylonitrile-1,3-butadiene (NBR or nitrile rubber), isobutylene-isoprene, cis-1,4-polyisoprene, 1,4-poly(1,3-butadiene), polychloroprene, and block copolymers of isoprene or 1,3-butadiene with styrene such as styrene-ethylene-butadiene-styrene (SEBS). In other embodiments, elastomers comprise polyalkene oxide polymers, acrylics, or polysiloxanes (silicones) or combinations thereof.

In a further embodiment, elastomers suitable for use in sintered polymeric materials of the present invention, in some embodiments, comprise FORPRENE®, LAPRENE®, SKYPEL®, SKYTHANE®, SYNPRENE®, RIMFLEX®, Elexar, FLEXALLOY®, TEKRON®, DEXFLEX®, Typlax, Uceflex, ENGAGE®, HERCUPRENE®, Hi-fax, Novalene, Kraton, Muti-Flex, EVOPRENE®, HYTREL®, NORDEL®, VITON®, Vector, SILASTIC®, Santoprene, Elasmax, Affinity, ATTANE®, SARLINK®, etc.

The sintered porous plastic nibs have a porosity of from about 20% to about 80%, from about 25% to about 70%, from about 30% to about 60%, or from about 30% to about 50%. The nibs have a pore size of from about 1 μm to about 200 μm, from about 10 μm to about 100 μm, or from about 20 μm to about 60 μm. Nibs may be hydrophobic or hydrophilic, and this property is chosen depending on the sample to be contacted with the nib. In one embodiment, the nibs are hydrophilic so that hydrophilic samples may be absorbed into the nib through a capillary force. Hydrophobic nibs may be used to collect non-aqueous based, low surface tension liquid samples. Exemplary nib shapes are described above.

Natural Polymer Nibs.

The nibs in this application can also be made from natural polymers, such as cellulose and cellulose derivatives. In another embodiment, the nibs can also be made from natural polymers, such as cellulose and cellulose derivatives, in combination with one or more plastics.

Metal Nibs

In another embodiment the nibs are made from metal, such as sintered porous metal, metal tubes or balls. The metal nibs may be made from a variety of metals such as steel, stainless steel, copper, titanium, nickel and their alloys.

In one specific embodiment, nibs are sintered metals.

The sintered metal nibs have a porosity of from about 20% to about 80%, from about 25% to about 70%, from about 30% to about 60%, or from about 30% to about 50%. The nibs have a pore size of from about 1 μm to about 200 μm, from about 10 μm to about 100 μm, or from about 20 μm to about 60 μm. Exemplary nib shapes are described above.

Ceramic Nibs

In another embodiment the nib can be made from ceramics, such as sintered porous ceramics, ceramic tubes or balls. The ceramic nibs may be made from a variety of ceramics, such as alumina, beryllia, ceria, zirconia, carbide, boride, nitride, or silicide.

In one specific embodiment, nibs are sintered porous ceramic.

The sintered ceramic nibs have a porosity of from about 20% to about 80%, from about 25% to about 70%, from about 30% to about 60%, or from about 30% to about 50%. The nibs have a pore size of from about 1 µm to about 200 µm, from about 10 µm to about 100 µm, or from about 20 µm to about 60 µm. Exemplary nib shapes are described above.

Glass Nibs

Another embodiment of this invention is that the nib can be made from glass, such as sintered porous glass, glass tubes or balls. The glass nibs may be made from a variety of glasses, such as sodium-lime glass, lead glass, borosilicate glass, aluminosilicate glass, fused silica glass and bioglass.

In one specific embodiment, nibs are sintered porous glass.

The sintered glass nibs have a porosity of from about 20% to about 80%, from about 25% to about 70%, from about 30% to about 60%, or from about 30% to about 50%. The sintered glass nibs have a pore size of from about 1 µm to about 200 µm, from about 10 µm to about 100 µm, or from about 20 µm to about 60 µm.

The nibs can be in many molded shapes, such as a sharp point, a round shape, a spherical shape or an angular shape, such as a triangular shape. The nibs can also be in fine tube form that can collect a sample through capillary force.

Plastic Fiber Nibs

In another embodiment, nibs are made from a variety of plastics fibers, such as continuous fibers or staple fibers. Continuous fibers and staple fibers can be monocomponent fibers and/or bicomponent fibers. Examples of monocomponent fibers include, but are not limited to, glass, polyethylene (PE), polypropylene (PP), polyacrylate, polyacrylic nitrile (PAN), polyamides (Nylons), polyethylene terephthalate (PET), polybutylene terephthalate (PBT), copolyester (CoPET). Plastic fiber nibs may further comprise cellulose based fibers such as cotton, rayon and Tencel. Examples of suitable bicomponent fibers include, but are not limited to, PE/PET, PP/PET, CoPET/PET, PE/Nylon, PP/Nylon, and Nylon-6,6/Nylon-6. Plastic fiber nibs may further comprise cellulose based fibers such as cotton, rayon and Tencel.

Fiber nibs can also be impregnated with other polymers to improve their strength, such as polymers including but not limited to thermosetting polyesters, phenolic resins, epoxy resins and urea resins.

In one specific embodiment, fiber nibs are made from a pultrusion process

The fiber nibs have a porosity of from about 4% to about 90%, from about 20% to about 80%, from about 30% to about 70%, or from about 40% to about 60%. The fiber nibs have a pore size of from about 1 µm to about 200 µm, from about 10 µm to about 100 µm, or from about 20 µm to about 60 µm.

Fiber nibs may be hydrophobic or hydrophilic, and this property is chosen depending on the sample to be contacted with the nib. In one embodiment, the fiber nibs are hydrophilic so that hydrophilic samples may be absorbed into the nib through a capillary force.

Figure 17:
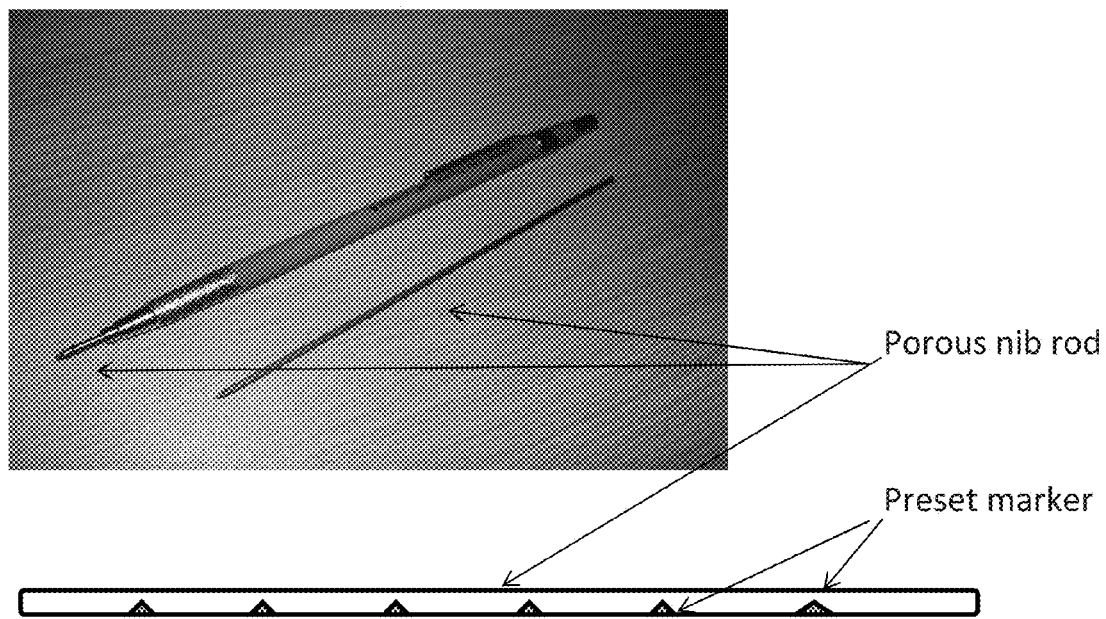
FIG. 17. Schematic representation of a nib in a rod form with indented markers. The indented marker can be preset breaking spots. The rod shape nib can move in and out of the device, and break into segments similar to a pencil lead in an automatic pencil, a mechanical pencil or a propelling pencil.

Exemplary nib shapes are described above. Fiber nibs may have different shapes, such as bullet head, chisel, etc. The shape can be cut or ground. The nib can be in a rod form with indented markers. The indented marker can be preset breaking spots. The rod shape nib can move in and out of the device, and break into segments similar to a pencil lead in an automatic pencil, a mechanical pencil or a propelling pencil (FIG. 17).

Properties of Nibs

A specific embodiment of this invention is that the amount of absorbed sample is controlled by the size and pore volume of the nib. In one specific embodiment, the sample volume is controlled by the size and void space in the hydrophilic region of the nibs. The nibs in the device may be used to deposit a sample on any desired surface.

Nibs may have different shapes chosen for particular applications. In one embodiment, the nib may be pyramidal in shape with the apex directed away from the base. In this manner, the point or apex may contact the sample and then may be placed in a mass spectrometer in a manner such that voltage is applied to the nib apex to release molecules into the mass spectrometer. In one embodiment, the present invention provides sintered porous plastic nibs or other porous nibs with at least one sharp point, for example for use in delivery of charged molecules to a mass spectrometer. In one embodiment the present invention provides sintered porous plastic nibs with at least one sharp point for generating an aerosol of charged molecules, such as difficult to vaporize biological molecules, for delivery to a mass spectrometer for measurement of the biological molecules. In one embodiment, air or a carrying gas may be passed through the sintered porous plastic nibs in combination with application of voltage to deliver charged molecules to a mass spectrometer.

In one embodiment, porous nibs are maintained in a dry condition. In another embodiment, porous nibs are maintained in a moist condition. In another embodiment, porous nibs are maintained in a moist condition. In another embodiment, porous nibs are contain a liquid.

The sample capacity of a nib may be from about 0.1 μl to about 500 μl, from about 1 μl to about 250 μl, from about 3 μl to about 200 μl, from about 5 μl to about 150 μl, or from about 10 μl to about 100 μl. The pore volume of a nib may be greater than about 1 μl or less than about 1000 μl, or any value between about 1 μl and about 1000 μl.

Porous nibs may be treated with plasma for surface activation. Plasma treatment, for example with oxygen plasma, can increase hydrophilicity of the nib. Plasma treatment can use any gas or combination of gases or vapors to provide plastic with hydrophilic properties. Plasma treatment may also be used in a cleaning process for the nibs.

Porous nibs may be treated with surfactants as known to one of ordinary skill in the art.

Porous nibs may be treated with polyelectrolyte solutions to increase hydrophilicity. In one embodiment, polyethyleneimine in aqueous or alcoholic solution may be applied to the nibs. Polyelectrolytes are polymers with electric charges in the polymer chain. The polyelectrolytes that may be used in this application include: one or more of a surfactant, phosphate, polyethylenimine (PEI), poly(vinylimidazoline), quaterized polyacrylamide, polyvinylpyridine, poly(vinylpyrrolidone), polyvinylamines, polyallylamines, chitosan, polylysine, poly(acrylate trialkyl ammonia salt ester), cellulose, poly(acrylic acid) (PAA), polymethylacrylic acid, poly(styrenesulfuric acid), poly(vinylsulfonic acid), poly(toluene sulfuric acid), poly(methyl vinyl ether-alt-maleic acid), poly(glutamic acid), dextran sulfate, hyaluric acid, heparin, alginic acid, adipic acid, or chemical dye. Polyelectrolyte-treated nibs may also receive additional treatments, such as exposure to surfactant solutions or heparin.

Functional Additives

Porous nibs may contain functional additives, including but not limited to the following: polyelectrolytes, C-18, C-8 or C-4 modified silica, silica gel, ion exchange material, controlled porous glass (CPG), solid phase extraction (SPE) media, cell lysis reagents, protein denaturing additives, chemicals that denature or de-activate proteins and/or lyse cells, anti-oxidants, chemicals that preserve the analyte to be measured in the sample, enzyme inhibitors, antimicrobials, and color change indicators, etc.

Porous nibs may contain functional additives such as anti-clotting agents, for example, heparin or warfarin, to retard blood clot formation. Such anti-clotting agents are known to one of ordinary skill in the art of handling blood samples.

Functional additives also include but are not limited to chelating agents, such as ethylene diaminetetraacetic acid (EDTA), surfactants, such as anionic surfactant, cationic surfactant or non-ionic surfactant, DNA stabilizing agents, such as uric acid or urate salt, or a weak acid, such as Tris(hydroxymethyl)aminomethane (TRIS). Functional additives also include but are not limited to a chaotropic agent, such as urea, thiourea, guanidinium chloride, or lithium perchlorate. Nibs may also contain an anti-coagulant, such as heparin, citrate and/or chelating agents.

A surfactant can be an anionic surfactant, for example sodium dodecylsulfate (SDS), sodium dodecyl sulfate (SDS), sodium dodecyl benzenesulfonate, sodium lauryl sarcosinate, sodium di-bis-ethyl-hexyl sulfosuccinate, sodium lauryl sulfoacetate or sodium N-methyl-N-oleoyltaurate, a cationic surfactant, such as cetyltrimethylammonium bromide (CTAB) or lauryl dimethyl benzyl-ammonium chloride, a non-ionic surfactant, such as nonyl phenoxypolyethoxyethanol (NP-40), Tween-20, Triton-100 or a zwitterionic surfactant, such as 3-[(3-Cholamidopropyl)dimethylammonio]-1-propanesulfonate (CHAPS). Fluorosurfactants may also be used, such as Zonyl® fluorosurfactant from DuPont. Other surfactants may be employed as known to one of ordinary skill in the art. Different surfactants can be combined together to obtain better hydrophilic results.

The stem portion of a porous plastic nib may contain color change indicators which change color upon contact with a sample, such as a liquid. By placing color change indicators at specific locations on the stem, the operator can observe the sample volume transported through the tip of the nib and into the nib stem. Color change indicators are disclosed in US 2008/0199363. This is particularly useful when using colorless or slightly colored samples.

These color change indicators are particles that are located in the sintered porous plastic matrix. These particles of color change indicators are added to the particles of plastic and mixed before sintering to form the sintered porous plastic matrix. These particles of color change indicators retain particulate characteristics in the sintered porous plastic matrix as they have a higher melting temperature than the plastic particles. When particles of color change indicators are employed, the sintering temperature is chosen to sinter plastic particles but not to melt the dye particles.

The functional additives in the nibs can be introduced by co-sintering, solution treatment or both.

In another embodiment, nibs may be used for applying a fluid to a surface. For example, a topical anesthetic, an antiseptic fluid, a wound care agent, an antibacterial, an antibiotic, betadine, povidone-iodine, detergent, an antiviral, a pharmaceutical, a nutraceutical or a skin care product such as a sun screen, moisturizer or insect repellant substance may be applied.

In another embodiment, nibs are sterilized. In yet another embodiment nibs are sterilized before or after surface activation. Sterilization may occur using techniques known to one of ordinary skill, such as gamma irradiation, plasma, ethylene oxide gas, dry heat or wet heat.

Manufacture of Nibs

In one embodiment, the porous nibs to be inserted in a device, such as a writing instrument-like device or pen-like device are generally comprised of two components, a nib tip and a nib stem, although in other embodiments, the tip may be inserted into a device without a nib stem. The nib tip contacts the sample and the nib stem is for inserting the nib into the device. In one embodiment, the nibs are made from molding process by placing plastic particles in a mold of desired shape and then sintering the mold using pressure and heat to form the nib.

The nib tip and nib stem may have the same chemical composition or different chemical compositions. In this embodiment, tips are used to collect, store, transport and/or deliver the samples and stems are use for connecting the tip to a housing. In another embodiment, tips are used to collect, store, transport and/or deliver the samples, and stems are use to connect the tip to a housing and also to collect, store, transport and/or deliver the samples.

For example, in one design, the nib tip may be formed of any of the above-described materials, and the nib stem, if provided, may be formed of a different material. The nib tip and nib stem may then be welded, sintered, adhered via adhesive, or any other appropriate securing mechanism may be used to secure the two components together. Alternatively, the two different materials may be placed in the same mold and sintered or heated so that they form an integral component. In another design, the nib stem, if used, may be formed of the same material as the nib tip, such that the entire structure may be formed integrally or the portions may be independently formed and then secured to one another using any of the above described options. In a further design, a nib stem is not used and the nib tip itself is designed such that it can be directly secured to the device. Based on this design, a nib may not have a stem and the whole nib is the tip, such as spherical, conical, triangular, cylindrical or other short or elongated nibs.

In one embodiment of sintered porous plastic nibs, the molding and sintering conditions to make sintered porous nibs depends on the polymer. One of ordinary skill in the art is familiar with the temperatures and pressures that are appropriate for specific polymers.

A representative method of making a single component nib follows. Plastic particles, in some embodiments, are sintered at a temperature ranging from about 200° F. to about 700° F. In other embodiments, plastic particles are sintered at a temperature ranging from about 300° F. to about 500° F. The sintering temperature, according to embodiments of the present invention, is dependent upon and selected according to the identity of the plastic particles.

Plastic particles, in some embodiments, are sintered for a time period ranging from about 30 seconds to about 30 minutes. In other embodiments, plastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of plastic particles is administered under ambient pressure (1 atm). In other embodiments sintering of plastic particles is administered under pressures greater than ambient pressure.

A representative method of making a dual component nib with a different nib tip and nib stem composition follows. The method generally includes (a) forming a porous nib and (b securing the porous nib to a pen-like housing. It may also include methods where forming the porous nib includes forming a porous nib having a nib tip and a nib stem and inserting the nib stem into an opening of the pen-like housing.

The first plastic particle mix is deposited in a tip portion of a mold, the second plastic mix is deposited in a stem portion of the mold adjacent to the first portion of the mold. Next the first plastic particle mix and second plastic particles mix are sintered to form the nibs containing a tip and a stem.

First plastic particles and second plastic particles, in some embodiments, have average sizes ranging from about 1 μm to about 1 mm. In another embodiment, first plastic particles and second plastic particles have average sizes ranging from about 10 μm to about 900 μm, from about 50 μm to about 500 μm, or from about 100 μm to about 400 μm. In a further embodiment, first plastic particles and second plastic particles have average sizes ranging from about 200 μm to about 300 μm. In some embodiments, first plastic particles and second plastic particles have average sizes less than about 1 μm or greater than about 1 mm. Sizes of first plastic particles, second plastic, in some embodiments, are selected independently.

First plastic particles and second plastic particles, in some embodiments, are sintered at a temperature ranging from about 200° F. to about 700° F. In some embodiments, first plastic particles and second plastic particles are sintered at a temperature ranging from about 300° F. to about 500° F. The sintering temperature, according to embodiments of the present invention, is dependent upon and selected according to the identity of the first plastic particles and second plastic particles.

First plastic particles and second plastic particles, in some embodiments, are sintered for a time period ranging from about 30 seconds to about 30 minutes. In other embodiments, first plastic particles and second plastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of first plastic particles and second plastic particles is conducted under ambient pressure (1 atm). In other embodiments sintering of first plastic particles and second plastic particles is conducted under pressures greater than ambient pressure.

A polymeric material, such as a nib, produced by sintering particles of first plastic particles and second plastic particles, in embodiments of the present invention, can comprise a tip region and a stem region, the tip region comprising the sintered first plastic particles or other additives, and the stem region comprising the sintered second plastic particles. The shape of the mold can be any desired shape allowing for the facile and single-step production.

Nibs can also be made from sintered porous metals, sintered porous glass and sintered porous ceramics. Sintered porous metals and similar products are sold by Mott Corporation (Farmington, Conn., USA 06032). Sintered porous glass and glass tubes and similar products are sold by Hilgenberg-GMBH (Malsfeld, Germany). Sintered porous ceramics and tubes and similar products are sold by CoorsTek (Golden, Colo., USA). Sintered metal, glass and ceramic nibs are made by putting the metal, glass or ceramic powder into a mold that results a nib shape, compressing the powder to form a part, then sintering the part in a oven to make the nib.

Fiber nibs can be made by the processes described in the U.S. Pat. No. 5,607,766 and US Patent Application 20020193030.

Examples of potential nib structures are shown in FIG. 1. Examples of nibs with tip and stem structure are shown in FIG. 2. In FIG. 2, position A is the nib tip, position B is the nib stem and position C is the break point if the nib is designed to be broken away from the stem for separation and further analysis.

In some embodiments nibs do not contain a stem structure. Some of these examples are shown in FIG. 1. In these cases, the nib chemistry and structure are generally uniform.

In the nibs of FIG. 2, tip A and stem B may have the same pore size or pore volume. Alternatively, tip A and stem B may have different pore sizes and pore volumes. Tip A and stem B may have different hydrophobicities. In one embodiment, tip A is hydrophilic and stem B is hydrophobic. In another embodiment, tip A is hydrophobic and stem B is hydrophilic. In another embodiment, tip A is hydrophobic and stem B is hydrophobic. In another embodiment, tip A is hydrophilic and stem B is hydrophilic.

Tip A may also contain functional additives, such as silica, C-4, C-8, C-18 silica, ion exchange, cell lysis and/or protein denaturing materials. Stem B may have a color changing material for liquid to indicate a change of color upon contact with a liquid. In another embodiment, stem B may contain functional additives, such as silica, C-4, C-8, C-18 silica, ion exchange, cell lysis and/or protein denaturing materials.

Tip A may contain chelating agents, such as ethylenediaminetetraacetic acid (EDTA), surfactants, such as anionic surfactants, cationic surfactants or non-ionic surfactants, DNA stabilizing agents, such as uric acid or urate salt, or a weak acid, such as Tris(hydroxymethyl)aminomethane (TRIS). Tip A may also contain chaotropic agents, such as urea, thiourea, guanidinium chloride, or lithium perchlorate. Tip A may also contain anti-coagulant, such as heparin, and citrate and chelating agents. A surfactant can be an anionic surfactant, for example sodium dodecylsulfate (SDS), sodium dodecyl sulfate (SDS), sodium dodecyl benzenesulfonate, sodium lauryl sarcosinate, sodium di-bis-ethylhexyl sulfosuccinate, sodium lauryl sulfoacetate or sodium N-methyl-N-oleoyltaurate, a cationic surfactant, such as cetyltrimethylammonium bromide (CTAB) or lauryl dimethyl benzyl-ammonium chloride, non-ionic surfactants, such as nonyl phenoxypolyethoxylethanol (NP-40), Tween-20, Triton-100 or a zwitterionic surfactant, such as 3-[(3-Cholamidopropyl)dimethylammonio]-1-propanesulfonate (CHAPS).

The nibs or the nib tips in this invention can absorb 1 μl, 2 μl, 5 μl, 10 μl, 20 μl, 50 μl, 100 μl, 200 μl, 500 μl, 1000 μl, 1500 μl, and up to 2000 μl liquid samples or any amount between 1 μl and 2000 μl. In one embodiment, the nibs or nib tips are designed for uptake of a predetermined amount of liquid.

Operation of the Nib with the Tip and Stem.

The nib tip (which may or may not be attached to a stem) is placed in contact with a sample. The sample is absorbed into the nib tip. The sample may flow through the nib tip and into the attached stem, if provided.

At this point, several options exist. The nib tip and nib stem may be covered and stored until the appropriate time to perform a test on the sample contained in either the nib tip or the nib stem. Alternatively, the nib tip and nib stem may be separated and stored individually until the appropriate time to perform an assay of one or more analytes in the sample.

The nib with tip and stem structure can be used as a whole. In this manner, the whole nib may be added to a device, such as a mass spectrometer (e.g., so that the porous nib is in proximity to a sample receiving chamber in the mass spectrometer), so that the mass spectrometer may measure aerosolized particles of the sample contained in the nib. This aerosolization may be achieved through a variety of means such as applying a voltage to the nib. In one embodiment, air or a carrying gas may be passed through the sintered porous plastic nibs in combination with application of voltage to aid aerosolization of charged molecules for delivery to a mass spectrometer. Laser energy may also be applied to aerosolize molecules to be detected, for example as in methods employing matrix-assisted laser desorption/ionization (MALDI). MALDI methods may be used in time of flight (TOF) mass spectrometers.

Alternatively, the whole nib may also be added to a receptacle such as a test tube, centrifuge tube or assay tube, and the sample may be processed, for example by eluting the sample for assay of an analyte. Such receptacles may also contain reagents useful in performing an assay of one or more analytes in the sample. Such reagents are known to one of ordinary skill in the art and are chosen based on the analyte to be measured. For example, analyte-specific antibodies, optionally in addition to a colorimetric indicator may be used to bind to a protein and develop a color.

The nib tip may be removed from the nib stem. For example, the nib tip may be pressed against a surface or a container wall with sufficient force to separate the nib tip from the tip stem. An individual skilled in the art of pipetting can easily apply sufficient force to separate the nib tip from the nib stem. In this manner, the nib tip may be added to a device such as a mass spectrometer, so that the mass spectrometer may measure aerosolized particles of the sample contained in the nib tip. This aerosolization may be achieved through a variety of means such as applying a voltage to the nib tip.

In another embodiment, the nib tip or nib stem may have indentations or other points of relative weakness compared to the non-indented regions. Such indentations may occur at predefined intervals in the length of the nib tip or nib stem. These indentations facilitate breakage of a subsection or segment of the nib tip or nib stem so that individual segments containing a sample of interest may be separated and analyzed independently.

Alternatively, the nib tip may also be added to a receptacle such as a test tube, centrifuge tube or assay tube and the sample may be processed, for example by eluting the sample for assay of an analyte. Such receptacles may also contain reagents useful in performing an assay of one or more analytes in the sample. Such reagents are known to one of ordinary skill in the art and are chosen based on the analyte to be measured. For example, analyte-specific antibodies, optionally in addition to a colorimetric indicator may be used to bind to a protein and develop a color.

Following separation of the nib tip from the nib stem, the nib stem can be stored to retain the sample for future verification purpose. In another embodiment, the stem may then be placed in another container so that the sample contained in the stem may be eluted from the stem for analysis of an analyte in the sample using an appropriate method. For example, in one embodiment, the sample may contain a protein or a peptide and the elution of the protein or the peptide from the stem makes the protein or peptide available for measurement with ELISA or RIA. In another embodiment, the stem may contain another type of biological molecule, such as a lipid, a nucleic acid (for example DNA or RNA), or a neurotransmitter (such as catecholamines, indoleamines, acetylcholine) or metabolite thereof.

A nib without a tip and a stem structure can be used as a whole piece in a similar way to a whole piece nib with a tip and a stem structure.

Device

Housing

Figure 7:
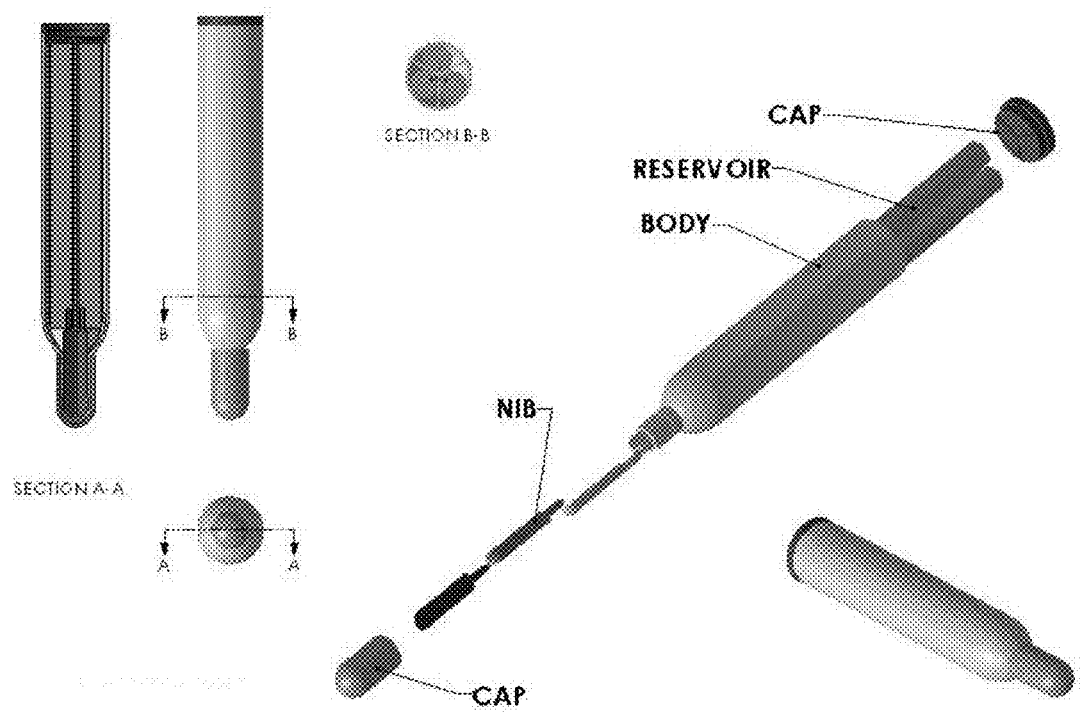
FIG. 7. Schematic representation of a pen structure with multiple nib structure.

The porous nib is generally contained or otherwise secured in a housing. In one embodiment, the housing is in a barrel shape similar to the shape of a pen. In one embodiment, the housing is electrically conductive. The housing will generally have an inner barrel, reservoir, or hollow portion and at least one end that is designed to receive a nib in use. The inner barrel may receive separate reservoir structures, if desired. As shown in FIG. 7, the housing may have a body, a reservoir, and a cap. The reservoir may be provided as a separate element or the reservoir may be built into the pen body. The use of the term "pen" in this invention is not intended to refer to a device for applying ink on a surface as a writing instrument, but is instead used to refer to a device which may be held like a pen and is used as a sample collection device. Exemplary pens are shown in FIGS. 7, 9-10, and 17.

Figure 6:
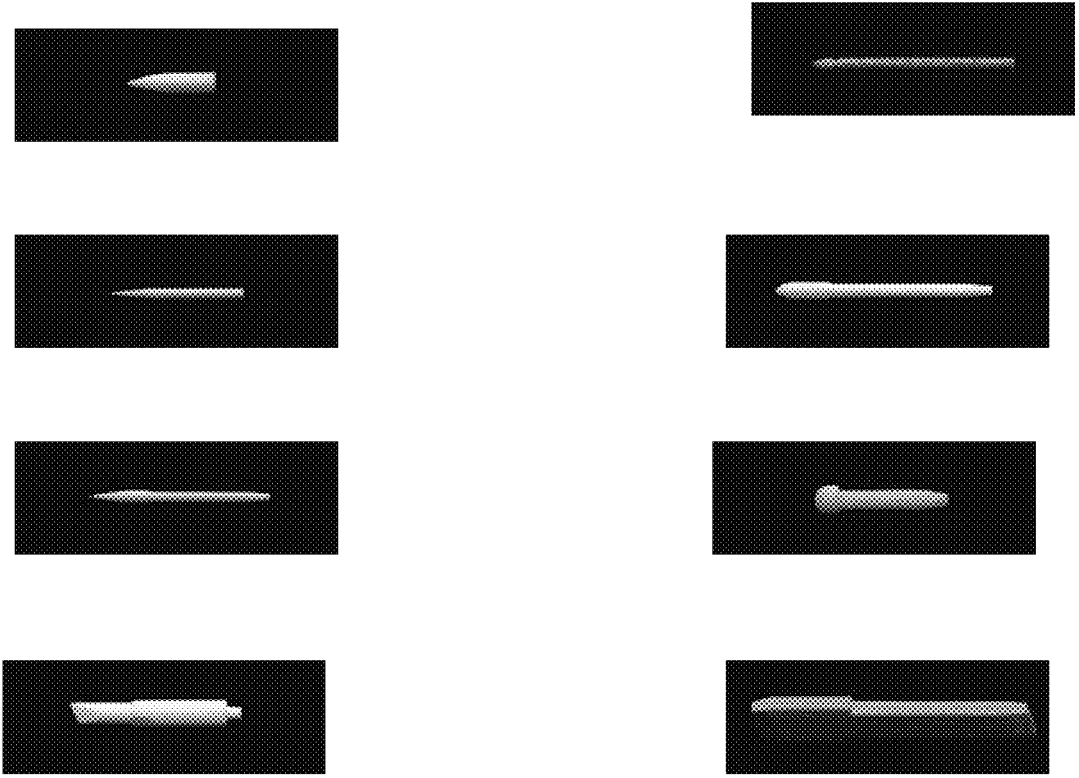
FIG. 6. Schematic representations of several shapes of nibs.

The pen has a nib (for collecting the sample) attached or otherwise secured at one or both ends and is contained in a housing. The nib may be friction fit into the pen housing, such that the nib may be pressed into an opening at an end of the pen and remain securely connected thereto. In another embodiment, the nib may be secured to (or formed with) a nib stem, which may then be friction fit into the pen housing. For example, the nib and/or the nib stem may have a geometry and shape that matches an internal barrel geometry and shape of the pen, such that the nib and/or nib stem can be securely connected within the pen. Examples of alternate nib stem shapes are illustrated by FIG. 6. The nib stems may have cross-sectional shapes that are generally round, square, flat or rectangular, star shaped, or any other appropriate shape. It is possible in this and other embodiments to provide a protrusion at the end of the nib stem that fits into a recess of the pen barrel or vice versa, such that an additional male/female connection secures the nib and/or nib stem in place.

A further embodiment is to secure the nib to the pen in such a way that allows it to be extended and retracted via depression of a button, much like a ball point pen. This can help protect the nib from external debris and/or from crushing its porous structure if a cap is not provided (or if the cap is not in place). (An example of this connection is described with respect to FIG. 10 below.) A further embodiment is to secure the nib to the pen in such a way that allows it to be extended from the pen via a series of clicks, much like a mechanical pencil. (An example of this connection is described with respect to FIG. 17 below.)

A further embodiment is to provide a ball and detent connection system on the nib stem and the pen, such that pressure on the ball causes a slight recess of the ball (whether on the nib stem or the pen) that allows it to be positioned in the detent recess (that is positioned on the other of the nib stem or the pen). Once the ball is slid into a detent; release of the ball causes it to sit firmly in the detent recess. A further connection method is to provide a J-slot connection, such that a protrusion fits into a J-shaped slot and locks the nib firmly in place. An alternate connection is to provide an outer base on the nib (or nib stem) that extends over an outer portion of the end of the pen in use, such that the nib acts like a cap positioned on the pen end. Any number of additional connection systems between the pen device and the nib and/or the nib stem are possible and are considered within the scope of this invention, and it should be understood that there are many ways to insert a nib into a housing to make the form of a pen. The above examples are illustrative only and are not intended to be limiting in any way.

Figure 8:
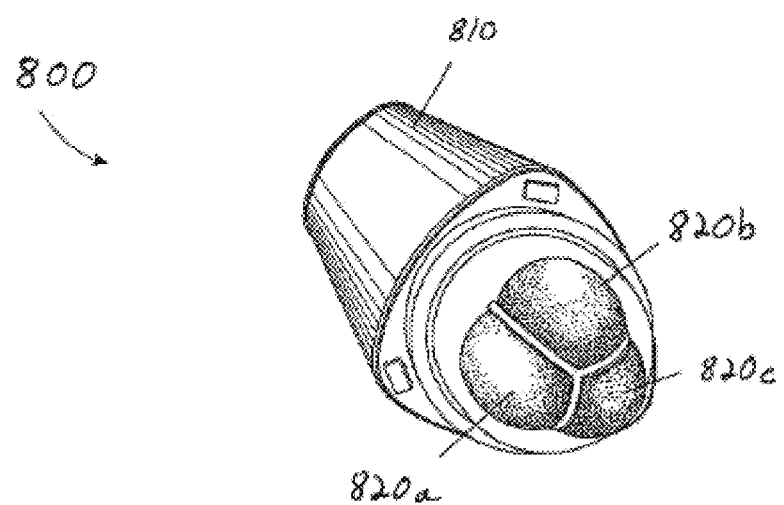
FIG. 8. Top view of a schematic representation of a pen 800 with a housing 810 containing multiple nibs 820a, 820b, 820c.

In one embodiment, a housing can contain more than one nib. The housing can be provided in many shapes, such as circular, oval, rectangular, or triangular. The corresponding nibs are generally similarly shaped. FIG. 8 illustrates a schematic representation of a pen 800 with a housing 810 containing multiple nibs 820a, 820b, 820c. These nibs may all be the same material or they may be different materials. Although nibs are shown as having rounded ends, it should be understood that multiple nibs have varying tip shapes may also be used. For example, multiple nibs with pointed ends may be desirable for certain sample collection scenarios.

Figure 9:
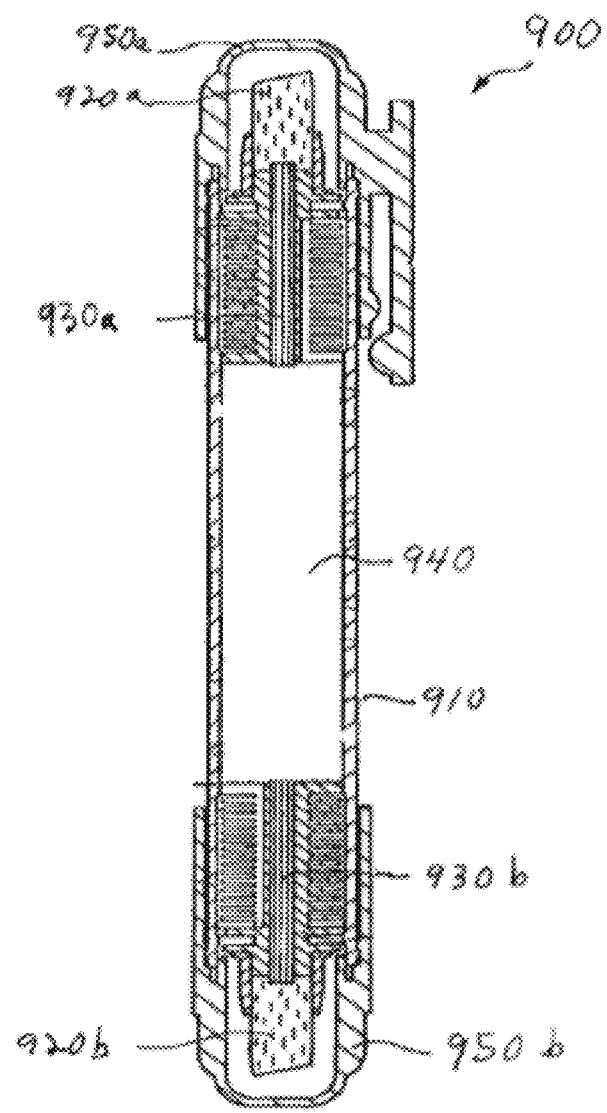
FIG. 9. Schematic representation of a typical pen structure 900 with a housing 910, nibs 920a, 920b on either end of the pen, nib stems 930a, 930b on either end of the pen, a reservoir 940, and caps 950a, 950b on either end of the pen.

FIG. 9 illustrates a pen structure 900 with a housing 910 having nibs 920a, 920b on either end of the pen. In this embodiment, each nib is secured to a nib stem 930a, 930b. Nib stems 930a and 930b are in fluid communication with a reservoir 940, which can be used to collect and store the collected sample. Once the sample has been collected, caps 950a, 950b are provided on either end of the pen, and can be positioned in order to prevent the nibs and the sample from drying out.

Figure 10:
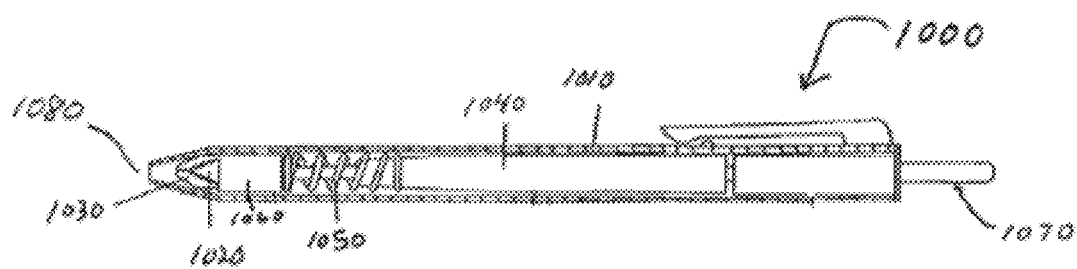
FIG. 10. Schematic representation of a typical press active pen structure 1000, with a housing 1010, retractable nib 1020, valve to open and close 1030, reservoir 1040, spring 1050, nib holder 1060, button 1070 for depressing the mechanism to push the nib through the opening 1080 in the tip of the pen.
Figure 11:
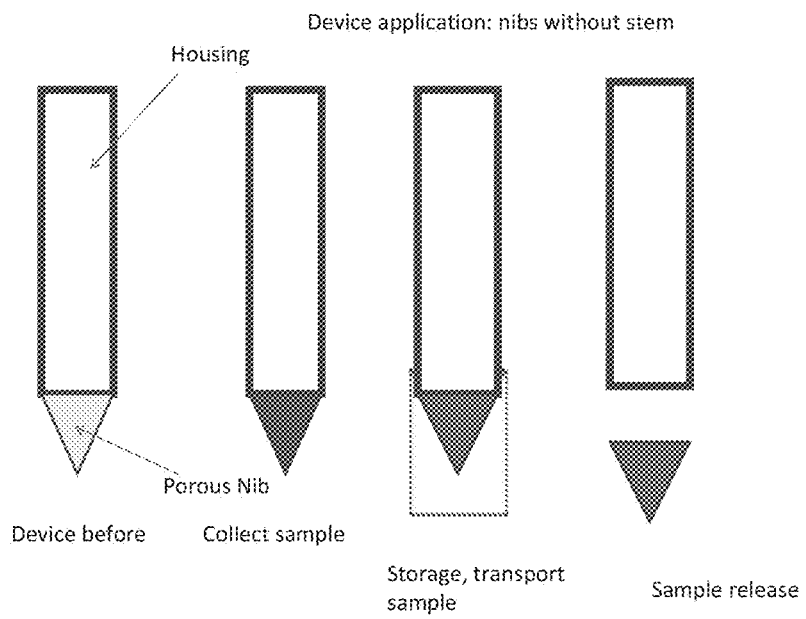
FIG. 11. Schematic representation of use of a device with a nib for sampling, storing/transporting and delivering the sample.
Figure 12:
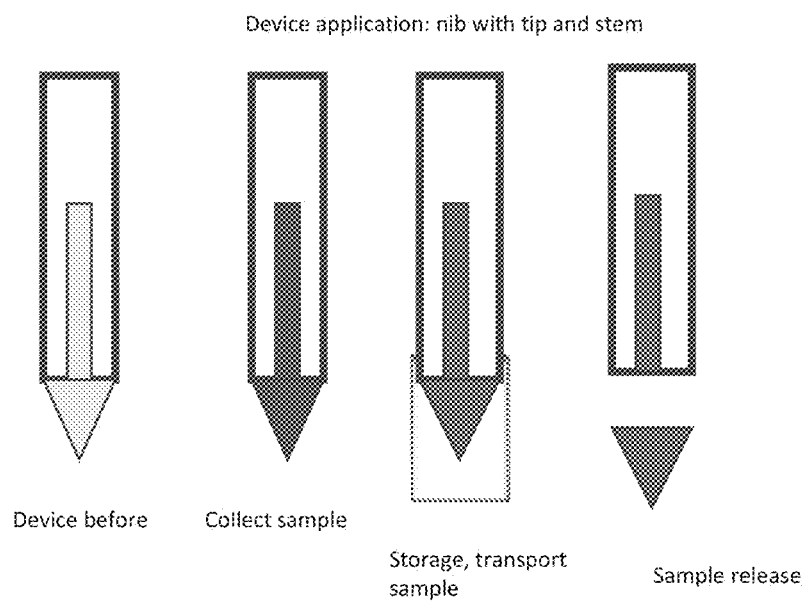
FIG. 12. Schematic representation of use of a device with a nib containing a tip and a stem for sampling, storing/transporting and delivering the sample.
Figure 13:
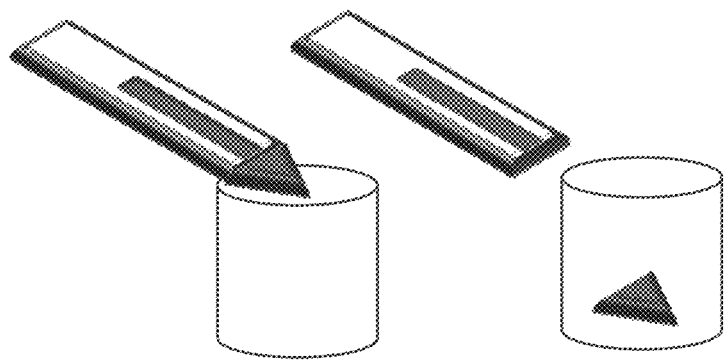
FIG. 13. Schematic representation of breaking the nib tip from the device and delivering the nib tip into a container.
Figure 14:
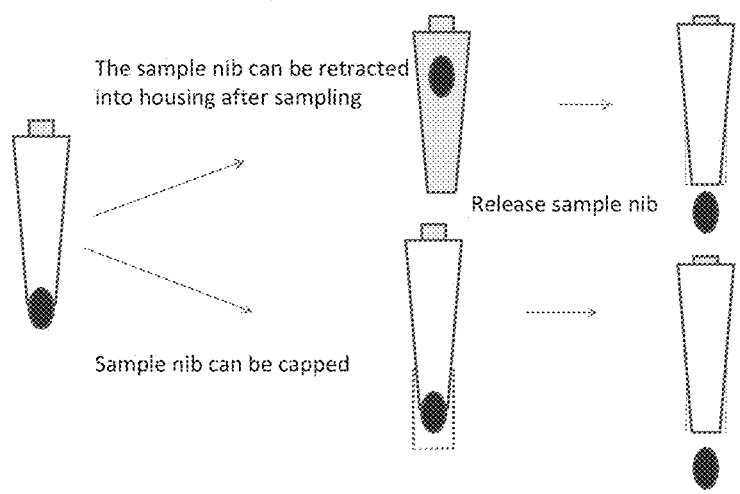
FIG. 14. Schematic representation of using a press active device for storing a sample nib inside the device chamber, or in the device tip and releasing the sample nib into a receptacle by pressing a button. Top: The device chamber contains chemicals for treating the sample nib. The nib is subsequently released into a receptacle for future testing. Bottom: The chamber is dry and the nib remains in the device tip and is capped (dotted lines). The nib is released into a receptacle when needed by pressing a button to release the nib.
Figure 15:
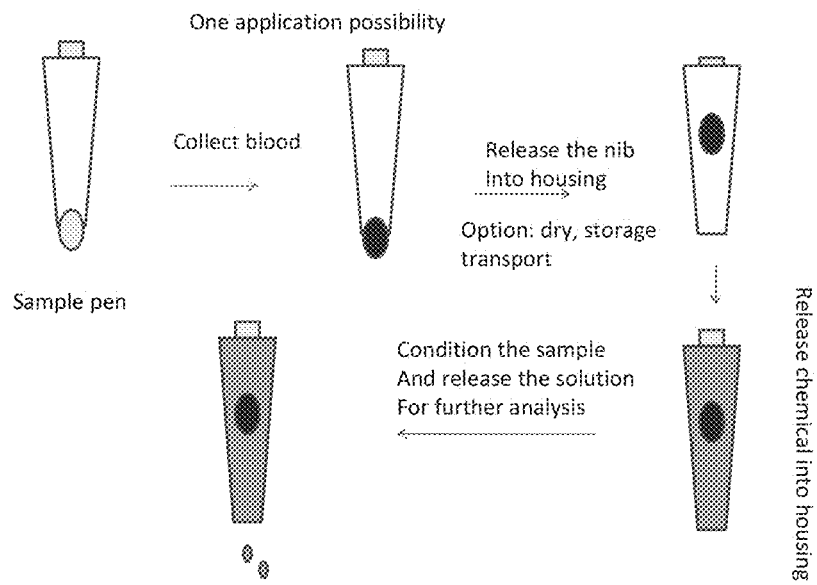
FIG. 15. Schematic representation of using a press active device for storing a sample nib inside the device chamber which contains a chemical to treat and extract the sample inside the nib, and releasing the extraction solution inside the chamber into a receptacle for analysis.
Figure 16:
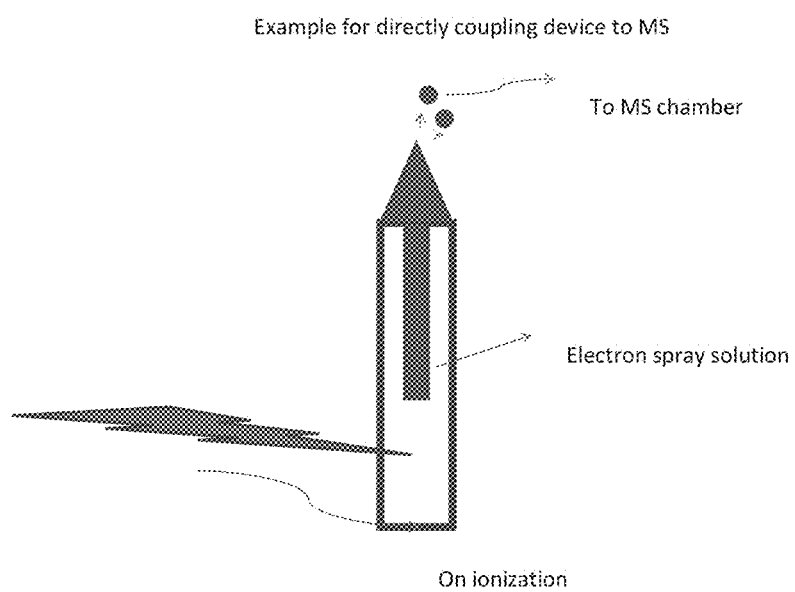
FIG. 16. Schematic representation of using a device for direct coupling to a mass spectrometer for measurement of an analyte inside the sample nib.

In one embodiment, the device may advance the nib from within the device by downwardly displacing the stem through mechanical means such as a piston, spring or other appropriate means known to one of ordinary skill in the art. For example, FIG. 10 illustrates a press active pen structure 1000, with a housing 1010, retractable nib 1020, an optional valve to open and close 1030 (in order to protect the nib from debris and drying out), reservoir 1040, spring 1050, nib holder 1060, and button 1070 for depressing the mechanism to push the nib through the opening 1080 in the tip of the pen. In use, depression of the button 1070 causes activation of the spring 1050, which causes movement of the nib holder 1060. Pressure of the nib holder 1060 against the valve 1030 causes the valve 1030 to open and the nib 1020 to extend from the opening of the pen. Retraction of the nib works similarly.

FIG. 17 illustrates an alternate nib advancement option. A button provided at one end of the pen allows a one-click motion to advance the nib outwardly from the opening at the desired length. This Figure also shows an embodiment of a nib in a rod form with one or more indented markers. The indented marker(s) can be preset breaking spots. These may be formed as slight indents where material is chiseled from the rod, they may be formed as lines of weakness where a material having a lesser strength is used, they may be formed as portions having more porosity and thus submit to easier breaking, or any other number of methods. The rod shaped nib can move in and out of the device as desired, and can break into segments similar to a pencil lead in an automatic pencil, a mechanical pencil or a propelling pencil.

In all of these embodiments, the general concept is to secure or otherwise retain the nib with respect to the pen such that the nib can be extended outside the housing body for use. In one embodiment the nib stem is inserted into or inside the housing body such that the nib tip is generally located outside the housing body, an example of which is shown in FIG. 7. The nib tip may be optionally covered with a cap when it is not in use. The nib is capped to prevent contamination before using. Before use, the cap is removed and the nib tip is applied to the sample and collects the sample by capillary action. The nib tip can then be covered with the cap when it is wet, or after the sample dries, depending on the application. In some embodiments, depending on the sample and analyte of interest, the nib may be maintained in a wet state. The cap may optionally contain desiccant, an oxygen scavenger or other materials for the purpose of sample preservation. The sample can be stored or transported for further analysis when desired. When further analysis is need, there are many ways to use this device. One option is to break the nib tip from the pen into another container for further purification, extraction and analysis. Another option is to release the entire nib into another container for further purification, extraction and analysis. In another embodiment, analysis occurs directly on the nib, for example by ionizing and aerosolizing the target molecules for analysis in a mass spectrometer (MS). This configuration can be also used for a nib without a stem. In yet another embodiment, voltage or current may be applied to the housing, particularly when the housing is electrically conductive, so that target molecules may be released from the nib in the housing for analysis in a mass spectrometer (MS). In one embodiment, air or a carrying gas may be passed through the sintered porous plastic nibs in combination with application of voltage to aid aerosolization of charged molecules for delivery to a mass spectrometer. Laser energy may also be applied to aerosolize molecules to be detected, for example as in methods employing matrix-assisted laser desorption/ionization (MALDI). MALDI methods may be used in time of flight (TOF) mass spectrometers.

In one embodiment, a housing can contain more than one nib. The housing can be in many shapes, such as circular, oval, rectangular, or triangular.

In one embodiment, the device is in a pen shape and has a housing, a nib and a cap. The nib position is fixed in the housing.

In one embodiment, the device may advance the nib from within the device by downwardly displacing the stem through mechanical means such as a piston, spring or other appropriate means known to one of ordinary skill in the art.

As described and shown, devices may contain one or more stem-nib combinations, each device containing a mechanism for separately advancing a nib from the tip of the device for contact with the sample, such as a separate shaft and spring mechanism. In this manner, a single nib may be advanced from the device to contact a sample.

The device mechanism for advancing the nib for contact of the nib with the sample may also contain a mechanism for retracting the nib back into the device after contact with the sample. After retracting the nib into the device, the opening of the device which transmitted the nib may be capped, thereby preventing evaporation of sample contained in the nib or contamination of the sample in the nib. This sample collection and storage device may be placed in the appropriate storage conditions until the operator decides to perform the sample analysis. This sample collection and storage device may be transported to another location. Devices may optionally contain a storage stabilizing agent, such as a desiccant or an oxygen scavenger. Alternatively the device may not be capped, thereby allowing the sample to dry on the nib and or the stem.

In another embodiment, the device may have one or more reservoirs which contain one or more chemicals useful for the purification and separation of an analyte in the sample contained in the nib. When the operator of the device chooses to use a reservoir, the fluid in the reservoir can contact the nib through a channel in the device. For example, the reservoirs may have wet chemicals and fluid in the reservoirs will not contact the nib until the operator pushes the reservoirs or a mechanism connected to the reservoirs to allow reservoir fluid to be delivered into the nib. The chemicals in the reservoirs can be purification solvents, reactive chemicals such as solvents, stabilization chemicals, oxygen scavengers, and growth media, protein precipitation agents or other sample treatment agents, sample detection or sample preservation reagents, etc. In another embodiment, the reservoirs are breakable chambers that contain chemicals. The chemical is released into the nib when needed by breaking the chambers with the nib through a mechanical engagement, for example with the stem of the nib breaking the end of the chamber, and permitting fluid flow through a channel into the nib or directly into the nib, in one embodiment by pushing a button.

In another embodiment, the device may have one or more dry reservoirs and the nib tip is connected to the dry reservoirs through the nib stem. When the nib tip contains a sample with target analytes requiring additional treatment before analysis, the nib tip is dipped into the treatment solution container, the treatment solution wicks through the tip and then moves into the one or more dry reservoirs. The sample containing the analyte in the nib tip is purified during the treatment solution wicking process and is ready for next analytical process.

In yet another embodiment, the nib in the device may function as both a sampling tip and a solution reservoir. When the sample tip contains target analytes requiring additional treatment before analysis, the nib tip is dipped into the treatment solution container, the treatment solution wicks through the tip and moves into the other end of the nib. The sample containing the analyte in the nib tip is purified during the treatment solution wicking process and is ready for next analytical process. The target analytes may be in the original sampling tip or at the other end of the nib depending on the solubility of the target analyte in the treatment solution.

The device may be coupled to other devices. In another embodiment, the device can be directly inserted into the chamber of a mass spectrometer through a connection means such as a port. This connection may take place using any appropriate connection or attachment system in order to locate the nib tip held by the device near a sample port in the mass spectrometer such that the molecules may be aerosolized from the nib tip and delivered into the mass spectrometer. Devices may have electrodes or a conductive wire, and electrical potential or current can be directly applied to the housing of the devices or to the nibs of the device for generating aerosol or electrochemical signals. In yet another embodiment, voltage or current may be applied to the housing, particularly when the housing is electrically conductive, so that target molecules may be released from the nib in the housing for introduction into a mass spectrometer (MS). In one embodiment, air or a carrying gas may be passed through the device and into the sintered porous plastic nibs in combination with application of voltage to aid aerosolization of charged molecules for delivery to a mass spectrometer.

The device may have a punch needle to puncture the sample, such as animal or human skin or other tissues or organs.

The punch needle can be a lancet and the lancet can be placed in different locations in the devices. For example, for a device having two ends, one end is the sampling nib and the other end is a lancet. In another embodiment, the device may also have a hollowed nib with a lancet located in the hollow channel of the hollowed nib.

Types of Samples

Samples include but are not limited to biological and non-biological fluids. Biological fluids include but are not limited to bodily fluids such as blood, plasma, urine, peritoneal fluid, pulmonary fluid, pericardial fluid, tears, saliva, cerebrospinal fluid, lymphatic fluids, gastrointestinal fluids, feces, fluids of the reproductive system, and amniotic fluid. Other biological fluids include but are not limited to culture medium such as cell or tissue culture medium. Non-biological fluids include water samples including fresh water, sea water, and wastewater samples, organic solution samples, inorganic solution samples, samples from the petrochemical industry such as samples from oil fields, environmental samples and food samples.

Samples also include but are not limited to tissues, animal or plant cells, microorganisms (for example, bacteria, viruses, mold, and fungi), and plasmids. Cells include but are not limited to cultured cells, epithelial cells, mesothelial cells, and endothelial cells. Cells may be obtained from tissues and organs using techniques known to one of ordinary skill in the art.

Target analytes include any desired analyte such as nucleic acid (DNA, RNA), carbohydrates, lipids, proteins, peptides, hormones, antibodies, metabolites, neurotransmitters, immunomodulators, drugs, drug metabolites, alcohol, ions, and electrolytes.

The present invention has applicability in a wide variety of fields including but not limited to pharmaceuticals, genomics, molecular biology, molecular diagnostics, DNA analysis for genetic identification of a sample and its origin, whole genome amplification, proteomics, forensic science, blood and tissue typing, toxicology, pharmacology, drug discovery, pharmacokinetics, plasmid screening, food and agricultural testing, animal identification, endocrinology, pregnancy testing, drug testing, and microbiology, In vitro diagnostic (IVD), home testing laboratory kits for example plasma glucose and insulin testing, etc, that require less sample, easy handling, storage, transportation, and accuracy sample measurement.

One specific application of present invention is to collect small volume blood samples from animals and humans for drug metabolic, pharmacokinetic (PK) and toxicokinetic (TK) investigations in the pharmaceutical industry.

Samples may also include non-biological samples, such as organic and inorganic samples. Such organic and inorganic samples include but are not limited to toxins, petrochemicals, and water.

The devices in this invention can be also used to collect, store, and transport bacteria and virus samples, for example bacteria and viruses in culture media.

Methods of Use

There are a number of ways that the device may be used. For example, the device may be used by contacting the porous nib with a liquid sample to be collected, and allowing the liquid sample to be absorbed into the porous nib. The sample may be allowed to dry on the porous nib or it may remain in its liquid form. Once the sample has been collected, it is possible to cap the nib and device, retract the nib into the device, or both. In one embodiment, the device is provided with a lancet for punching the skin. In this instance, the methods steps for use include: (a) piercing skin of an animal or mammal with the lancet to release blood; (b) contacting the blood with the porous nib; (c) allowing the blood to be absorbed into the porous nib; (d) allowing the blood to dry on the porous nib; and, (e) capping the porous nib in the device housing. Other methods of use include releasing the porous nib into a container; extracting an analyte from the nib with a solvent or a solution; and detecting the extracted solution for analysis of selected analytes. Further methods include the use of mass spectrometry to detect the targeted analyte in the extracted solution. In instances where the sample has been dried, the methods may include: (a) wetting the porous nib containing the dried sample with a solution; (b) applying an electrical potential to the wet porous nib; and (c) detecting ionized analytes released from the wet porous nib using a mass spectrometer. Alternatively, methods may include (a) wetting the porous nib containing the dried sample with a solution; (b) applying the wet porous nib to a surface in order to transfer sample from the wet porous nib to the surface; (c) introducing the surface into the mass spectrometer, and (d) detecting ionized analytes released from the surface using the mass spectrometer.

In one embodiment, the device is used with a MALDI TOF mass spectrometer. The nib containing analytes is rewetted with MALDI matrix solution. The matrix solution generally consists of crystallized molecules, of which the three most commonly used are 3,5-dimethoxy-4-hydroxycinnamic acid (sinapinic acid), α-cyano-4-hydroxycinnamic acid (alpha-cyano or alpha-matrix) and 2,5-dihydroxybenzoic acid (DHB). A solution of one of these molecules is made, often in a mixture of highly purified water and an organic solvent (normally acetonitrile (ACN) or ethanol). Trifluoroacetic acid (TFA) may also be added. An example of a matrix-solution is 20 mg/mL sinapinic acid in ACN:water:TFA (50:50:0.1). Next, the matrix solution in the nib is applied to a MALDI plate. The plate is then dried and ready for MALDI TOF MS analysis.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Sample Collection, Storage, Transportation and Delivery Device with Sintered Polyethylene Nib A device with a pen shape contains a pyramidal-shaped sintered porous polyethylene nib with a sharp apex. The polyethylene porous nib has average pore size of 25 μm and about 40% porosity. The nib is designed to take up 25 μl of liquid. The nib is pure polyethylene and free of additives that may affect future assays. The nib is preferably plasma treated for improved hydrophilicity.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 μl rat blood sample. The nib is left open to the atmosphere until the sample dries and is then capped for storage and possible transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 2

Sample Collection, Storage, Transportation and Delivery Devices with Sintered Polyethylene Nib A device with a pen shape contains a pyramidal-shaped sintered porous polyethylene nib with a sharp apex. The polyethylene porous nib has average pore size of 25 μm and about 40% porosity. The nib is designed to take up 25 μl of liquid. Other than polyethylene, the nib also contains EDTA, sodium dodecyl sulfate (SDS) and uric acid for sample preservation.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 μl rat blood sample. The nib is left open to the atmosphere until the sample dries and is then capped for storage and possible transport. When the sample needs to be tested, the cap is removed and nib is released from the pen into a receptacle. The dry nib with original blood sample is now ready for further testing. The device provides precise sampling (sample size is determined by the nib size) and ease of use. The device also prevents contamination, and provides a stable way to collect, store and transport biological samples.

EXAMPLE 3

Sample Collection, Storage, Transportation and Delivery Devices with Sintered Polypropylene Nib A device with a pen shape contains a pyramidal-shaped sintered porous polypropylene nib with a sharp apex. The polypropylene porous nib has average pore size of 90 μm and about 40% porosity. The nib is designed to take up 50 μl of liquid. The nib is preferably plasma treated for improved hydrophilicity.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains 50 μl of a rat blood sample. The nib is left open to the atmosphere until the sample dries and is then capped for storage and possible transport. When the sample needs to be tested, the cap is removed and nib is released from the pen into a receptacle. The device provides precise sampling (sample size is determined by the nib size) and ease of use. The device also prevents contamination, and provides a stable way to collect, store and transport biological samples.

EXAMPLE 4

Sample Collection, Storage, Transportation and Delivery Devices with Sintered Poly(Vinylidene Fluoride) Nib A device with a pen shape contains a long triangular-shaped sintered porous poly(vinylidene fluoride) (PVDF) nib with a sharp apex. The PVDF porous nib has an average pore size of 30 μm and about 50% porosity. The nib is designed to take up 25 μl of liquid. The nib is pure PVDF and free of additives that may affect assays. The nib is preferably plasma treated for improved hydrophilicity.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 μl rat blood sample. The nib is left open to the atmosphere until the sample dries and is then capped for storage and possibly transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 5

Sample Collection, Storage, Transportation and Delivery Devices with Sintered Polyamide (Nylon) Nib A device with a pen shape contains a long triangular-shaped sintered porous polyamide (Nylon) nib with a sharp apex. The nylon porous nib has average pore size of 20 µm and about 40% porosity. The nib is designed to take up 25 µl of liquid. The nib is pure Nylon and free of additives that may affect assays. The nib is preferably plasma treated for improved hydrophilicity.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 µl rat blood sample. The nib is left open to the atmosphere until the sample dries and is then capped for storage and possibly transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 6

Sample Collection, Storage, Transportation and Delivery Devices with Sintered Poly(Tetrafluoro Ethylene) Nib A device with a pen shape contains a long triangular-shaped sintered porous poly(tetrafluoroethylene) (PTFE) nib with a sharp apex. The PTFE porous nib has average pore size of 35 µm and about 50% porosity. The nib is designed to take up 25 µl of liquid. The nib may have surfactant for improved hydrophilicity.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 µl rat blood sample. The nib is left open to the atmosphere until the sample dries and is then capped for storage and possible transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 7

Sample Collection, Storage, Transportation and Delivery Devices with Polyacrylic Fiber Nib A device with a pen shape contains a long triangular-shaped sintered porous polyacrylic fiber nib with a sharp apex. The polyacrylic fiber nib has average porosity over 60% porosity. The nib is designed to take up 50 µl of liquid.

A 150 gm rat is injected with a drug and blood is sampled over time to examine the concentration of the drug and its metabolites in order to establish a pharmacokinetic profile.

The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains 50 µl of a rat blood sample. The nib is left open to the atmosphere until the sample dries and is then capped for storage and possible transport. When the sample needs to be tested, the cap is removed and nib is released from the pen into a receptacle. The device provides precise sampling (sample size is determined by the nib size) and ease of use. The device also prevents contamination, and provides a stable way to collect, store and transport biological samples.

EXAMPLE 8

Sample Collection, Storage, Transportation and Delivery Devices with Sintered Stainless Steel Nib A device with a pen shape contains a long triangular-shaped sintered porous stainless steel nib with a sharp apex. The stainless steel porous nib has average pore size of 20 µm and about 40% porosity. The nib is designed to take up 25 µl of liquid. The nib is pure stainless steel and free of additives that may affect assays.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it is full. When the nib is full, the nib contains a 25 µl rat blood sample. The nib is left open to the atmosphere until the sample dries and is then capped for storage and possible transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 9

Sample Collection, Storage, Transportation and Delivery Devices with Sintered Ceramic Nib A device with a pen shape contains a long triangular-shaped sintered porous ceramic nib with a sharp apex. The ceramic porous nib has average pore size of 10 µm and about 40% porosity. The nib is designed to take up 25 µl of liquid. The nib is pure ceramic and free of additives that may affect future assays.

A 150 gm rat is injected with a drug and blood is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it full. When the nib is full, the nib contains a 25 µl rat blood sample. The nib is left open to the atmosphere until the sample dries and is then capped for storage and possible transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 10

Sample Collection, Storage, Transportation and Delivery Devices with Sintered Polyethylene Nib with Tip and Stem Structure A device with a pen shape containing a long triangular-shaped sintered porous polyethylene nib with a sharp apex. The polyethylene porous nib has average pore size of 20 µm and about 40% porosity. The nib tip is designed to take up 25 µl of liquid and nib stem is designed to hold 50 µl of liquid. The nib is pure polyethylene and free of additives that may affect future assays. The nib is preferably plasma treated for improved hydrophilicity. A sample of blood is taken from a rat. The pen is used to advance the nib in order to contact the blood. The apex of the nib contacts the blood which is absorbed by capillary action into the nib until it is full. When the nib is full, the nib tip contains 25 µl of the rat blood sample and stem contains 50 µl of the rat blood sample. The nib is left open until dried and then capped for storage and possible transport. When the sample needs to be tested, the cap is removed and nib tip is released from the pen into a receptacle. The dry nib with the original 25 µl blood sample now is ready for further analysis. The 50 µl blood sample in the stem is retained for further testing. The stem may have clear marks for future division of the stem into segments for separate analyses. The device provides precise sampling (sample size is determined by the nib size) and ease of use. The device also prevents contamination, and provides a stable way to collect, store and transport biological samples.

EXAMPLE 11

Sample Collection, Storage, Transportation and Delivery Devices with Sintered Polyethylene Nib with C-18 Silica A device with a pen shape contains a cone-shaped sintered porous polyethylene nib with a sharp apex. The polyethylene porous nib has an average pore size of 20 µm and about 40% porosity. Other than polyethylene, the nib is also comprised of 40% C-18 silica particles. The nib is designed to take up 100 µl of liquid. The nib also contains a small amount of surfactant for improved hydrophilicity. The pen is used to advance the nib in order to contact the liquid. The apex of the nib contacts the liquid which is absorbed by capillary action into the nib until it is full. When the nib is full, the nib tip contains 100 µl of liquid sample. The nib is left open until dried and then capped for storage and possible transport. When the sample needs to be tested, the cap is removed and nib tip is released from the pen into a receptacle. The device provides precise sampling (sample size is determined by the nib size) and ease of use. The device also prevents contamination, and provides a stable way to collect, store and transport liquid samples, for example biological samples.

EXAMPLE 12

Sample Collection and Purification Devices with a Sintered Polyethylene Nib Containing C-18 Silica and a Dry Reservoir A device with a pen shape contains a cone-shaped sintered porous polyethylene nib with a sharp apex. The polyethylene porous nib has an average pore size of 20 µm and about 40% porosity. Other than polyethylene, the nib is also comprised of 40% C-18 silica particles. The nib is designed to take up 100 µl of liquid. The nib may also contain a small amount of surfactant for improved hydrophilicity. The pen is used to advance the nib in order to contact the liquid. The apex of the nib contacts the liquid which is absorbed by capillary action into the nib until it is full. When the nib is full, the nib contains 100 µl of liquid sample. After the sample is taken, the dry reservoir is engaged with the nib and pen nib can be dipped into a washing solution and the solution will continuously wick through the nib and reach the reservoir. Unwanted materials will be washed into the reservoir while concentrated and purified target analytes remain in the nib. Then the nib with purified sample now is ready for further testing. This device provides an easy way to collect and purify a liquid sample.

EXAMPLE 13

Sample Collection and Purification Devices with a Sintered Polyethylene Nib Containing Controlled Porous Glass (CPG) and a Dry Reservoir A device with a pen shape contains a cone-shaped sintered porous polyethylene nib with a sharp apex. The polyethylene porous nib has an average pore size of 20 µm and about 40% porosity. Other than polyethylene, the nib is also comprised of 30% CPG particles. The nib is designed to take up 100 µl of liquid. The nib may also contain a small amount of surfactant for improved hydrophilicity. The pen is used to advance the nib in order to contact the liquid. The apex of the nib contacts the liquid which is absorbed by capillary action into the nib until it full. When the nib is full, the nib contains 100 µl of liquid sample. After the sample is taken, the dry reservoir is engaged with the nib and pen nib can be dipped into a washing solution, the solution will continuously wick through the nib and reach the reservoir. Unwanted materials will be washed into the reservoir and concentrated while purified target molecules remain in the nib. Then the nib containing the purified sample now is ready for further testing. This device provides an easy way to collect and purify a liquid sample.

EXAMPLE 14

Sample Collection and Purification Devices with a Sintered Polyethylene Nib Containing Ion Exchange Resin and a Dry Reservoir A device with a pen shape contains a cone-shaped sintered porous polyethylene nib with a sharp apex. The polyethylene porous nib has an average pore size of 40 µm and about 40% porosity. Other than polyethylene, the nib is also comprised of ion exchange resin particles. The nib is designed to take up 100 μl of liquid. The nib also contains a small amount of surfactant for improved hydrophilicity. The pen is used to advance the nib in order to contact the liquid. The apex of the nib contacts the liquid which is absorbed by capillary action into the nib until it is full. When the nib is full, the nib contains 100 μl of liquid sample. After the sample is taken, the dry reservoir is engaged with the nib and the pen nib can be dipped into washing solution, the solution will continuously wick through the nib and reach the reservoir. Unwanted materials will be washed into the reservoir while concentrated and purified target analytes remain in the nib. Then the nib with purified sample now is ready for further testing. This device provides an easy way to collect and purify a liquid sample.

EXAMPLE 15

Sample Collection, Storage, Transportation and Delivery Devices with Sintered Polyethylene Nib Containing C-18 Silica and a Wet Reservoir A device with a pen shape contains a cone-shaped sintered porous polyethylene nib with a sharp apex. The polyethylene porous nib has an average pore size of 20 μm and about 40% porosity. Other than polyethylene, the nib is also comprised of 40% C-18 silica particles. The nib is designed to take up 100 μl of liquid. The nib also contains a small amount of surfactant for improved hydrophilicity. The pen is used to advance the nib in order to contact the liquid. The apex of the nib contacts the liquid which is absorbed by capillary action into the nib until it is full. When the nib is full, the nib tip contains 100 μl of liquid sample. The nib is left open until dried and then capped for storage and possible transport. When the sample needs to be tested, the cap is removed and wet reservoir is engaged with the nib. The solution inside the wet reservoir releases from the reservoir, wicks through the porous nib and carries the sample in the nib with the solution. The solution is tested for the target molecules. The device provides precise sampling (sample size is determined by the nib size) and ease of use. The device also prevents contamination, and provides a stable way to collect, store and transport liquid samples, for example biological samples.

EXAMPLE 16

Sample Collection, Storage, Transportation and Delivery Devices with Sintered Porous Spherical Nib A device with a pen shape contains a spherical-shaped sintered porous polyethylene (30%) and polypropylene (70%) nib (wt %). The sintered porous nib has an average pore size of 75 μm and about 40% porosity. The nib is designed to take up 25 μl of liquid. The nib is preferably plasma treated for improved hydrophilicity.

A 150 gm rat is injected with a drug and is sampled over time to examine the concentration of the drug and its metabolites in order to establish a pharmacokinetic profile. The rat is anesthetized and its tail vein is used to obtain a sample of blood. The pen is used to advance the nib in order to contact the blood. The apex of the nib contacts the blood which is absorbed by capillary action into the nib until it full. When the nib is full, the nib contains a 25 μl rat blood sample. The nib is left open to the atmosphere until the sample dries and is then capped for storage and possibly transport. When the sample needs to be tested, the cap is removed and nib is released from the pen into a receptacle. The dry nib with original blood sample now is ready for further testing. The device provides precise sampling (sample size is determined by the nib size) and ease of use. The device also prevents contamination, and provides a stable way to collect, store and transport biological samples.

EXAMPLE 17

Sample Collection, Storage, Transportation And Delivery Devices With Sintered Porous Long Rod Nib A device with a pen shape contains a 2 mm wide and 10 cm long rod-shaped sintered porous polyethylene nib. The sintered porous nib has an average pore size of 25 μm and about 60% porosity. The rod-shaped nib is designed to take up 10 μl of liquid in 5 mm of length. The nib is preferably plasma treated for improved hydrophilicity. The pen is used to advance the long rod nib in order to contact the blood. The nib contacts the blood which is absorbed by capillary action into the nib until it is full. When the nib is full, the nib contains a total of 200 μl blood. The long rod nib is left open until the sample dries and is then retracted into the pen and capped for storage and possible transport. When the sample needs to be tested, the cap is removed and nib is released from the pen into a receptacle. The long rod nib is pre marked with break points every 5 mm in length. The long rod nib can be divided into segments placed into different receptacle containers for multiple assays. The dry nib with the original blood sample now is ready for further testing. The device provides precise sampling (sample size is determined by the nib size) and ease of use. The device also prevents contamination, and provides a stable way to collect, store and transport biological samples.

EXAMPLE 18

Device for Delivery of the Sample to Mass Spectrometer

The device described in any one of examples 1-16 is mounted into a mass spectrometer. The nib is saturated with 50% water and 50% acetonitrile (ACN) solution that either contains $NH_4OH$ or formic acid. An electrical potential is applied to the nib through the pen and a carry gas is move through the nib. This process generates a finely charged aerosol for direct mass spectrometer measurement on the sample stored in the nib. This process significantly reduces the complexity of sample preparation for mass spectrometry.

EXAMPLE 19

Device for Use in Sample Collection and Delivery of the Sample to a Mass Spectrometer and Other Assay Equipment A device with a pen shape containing a pyramidal-shaped nib with a sharp apex and removably attached stem is used in this example to sample blood. A 150 gm rat is injected with a drug and blood is sampled over time to examine the concentration of the drug and its metabolites in order to establish a pharmacokinetic profile. The rat is anesthetized and its tail vein is used to obtain a 25 μl sample of blood. The pen is used to advance the nib in order to contact the blood. The apex of the nib contacts the blood which is absorbed by capillary action into the nib and then into the stem. When the stem is full, the nib tip is pressed against a receptacle used to introduce the nib tip into a mass spectrometer. The apex of the nib tip is then subjected to an electron spray to ionize the blood sample which is then introduced into the mass spectrometer for analysis. The drug and its metabolites are measured.

The stem is then placed into a test tube for subsequent analysis of the pituitary hormones prolactin and adrenocorticotrophic hormone (ACTH), suspected of being released by the injected drug. This hormone analysis is performed using techniques known to one of ordinary skill in the art, such as ELISA or radioimmunoassay.

Another pen is used at each subsequent sampling of the rat tail vein. A pharmacokinetic profile for the drug, its metabolites, prolactin and ACTH is established. The rat experiences minimal blood loss.

EXAMPLE 20

Sintered Porous Sampling Nib

Powdered polyethylene having an average particle size of about 150 µm was filled into cavities of an aluminum mold with vibration, heated to 350° F. for about three minutes and subsequently cooled to room temperature in about five minutes. The sintered porous polyethylene nibs had an average pore size of about 30 µm and porous volume of about 40%.

EXAMPLE 21

Sintered Porous Sampling Nib

Powdered UHMWPE polyethylene having an average particle size of about 30 µm was filled into cavities of an aluminum mold with vibration, heated to 350° F. for about three minutes and subsequently cooled to room temperature in about five minutes. The sintered porous UHMWPE polyethylene sampling nibs had an average pore size of about 10 µm and porous volume of about 40%.

EXAMPLE 22

Sintered Porous Sampling Nib

Powdered high density polyethylene having an average particle size of about 300 µm was filled into cavities of an aluminum mold with vibration, heated to 350° F. for about three minutes and subsequently cooled to room temperature in about five minutes. The sintered porous high density polyethylene sampling nibs had an average pore size of about 80 µm and porous volume of about 40%.

EXAMPLE 23

Sintered Porous Sampling Nib

Powdered polystyrene having an average particle size of about 180 µm was filled into cavities of an aluminum mold with vibration, heated to 370° F. for about three minutes and subsequently cooled to room temperature in about five minutes. The sintered porous polystyrene sampling nibs had an average pore size of about 45 µm and porous volume of about 40%.

EXAMPLE 24

Hydrophilic Sintered Porous Sampling Nib

Sintered porous sampling nibs from examples 20-23 were treated with low pressure plasma. The sample nibs were treated with oxygen plasma at 100 millitor (mtorr) and 100 watts (W) for 10 minutes in a plasma machine (Europlasma, Oudenaards, Belgium). The nibs became hydrophilic and adsorbed 20 µl deionized water in less than 3 seconds when 20 µl deionized water was placed on the tip of the nib with a pipette.

EXAMPLE 25

Hydrophilic Sintered Porous Sampling Nib

Sintered porous sampling nibs from examples 20-23 were treated with surfactants. The sample nibs were immersed in a solution comprising 79% deionized water, 20% isopropyl alcohol and 1% Tween® 20 at room temperature for 12 hours and dried at 70° F. for 8 hours in an oven. The nibs became hydrophilic and adsorbed 20 µl deionized water in less than 3 seconds when 20 µl deionized water was placed on the tip of the nib with a pipette.

EXAMPLE 26

Sintered Hydrophilic Porous Sampling Nib Comprising Dry Anionic Surfactants

A powdered mixture comprising 99.7% of polyethylene powders having an average particle size of about 160 µm and 0.3% of sodium N-methyl-oleoyltaurate (wt %) was filled into cavities of an aluminum mold with vibration, heated to 350° F. for about three minutes and subsequently cooled to room temperature in about five minutes. The sintered porous polyethylene sampling nibs had an average pore size of about 30 µm and porous volume of about 40%. The nibs were hydrophilic and adsorbed 20 µl deionized water in less than 3 seconds when 20 µl deionized water was placed on the tip of the nib with a pipette.

EXAMPLE 27

Sintered Hydrophilic Porous Sampling Nib Comprising Dry Anionic Surfactants

A powdered mixture comprising 99.5% of UHMWPE polyethylene having an average particle size of about 30 µm and 0.5% of sodium dodecyl sulfate (SDS) powder is filled into the cavities of an aluminum mold, heated to 350° F. for about three minutes and subsequently is cooled to room temperature in about five minutes. The sintered porous UHMWPE polyethylene sampling nibs have an average pore size of about 10 µm and porous volume of about 40%. The nibs are hydrophilic and adsorb 20 µl deionized water in less than 3 seconds when 20 µl deionized water is placed on the tip of the nib with a pipette.

EXAMPLE 28

Sintered Hydrophilic Porous Sampling Nib Comprising Dry Cationic Surfactants

A powdered mixture comprising 99% of polyethylene powders having an average particle size of about 150 µm and 1% of cetyltrimethylammonium bromide (CTAB) is filled into the cavities of an aluminum mold, heated to 350° F. for about three minutes and subsequently cooled to room temperature in about five minutes. The resulting sintered porous polyethylene sampling nibs have an average pore size of about 30 µm and porous volume of about 40%. The nibs are hydrophilic and adsorb 20 µl deionized water in less than 3 seconds when 20 µl deionized water is placed on the tip of a nib with a pipette.

EXAMPLE 29

Sintered Hydrophilic Porous Sampling Nib Comprising Dry Cationic Surfactants

A powdered mixture comprising 99% of UHMWPE polyethylene having an average particle size of about 30 µm and 1% of cetyltrimethylammonium bromide (CTAB) is filled into the cavities of an aluminum mold, heated to 350° F. for about three minutes and subsequently cooled to room temperature in about five minutes. The sintered porous UHMWPE polyethylene sampling nibs have an average pore size of about 10 µm and porous volume of about 40%. The nibs are hydrophilic and adsorb 20 µl deionized water in less than 3 seconds when 20 µl deionized water is placed on the tip of a nib with a pipette.

EXAMPLE 30

Hydrophilic Sintered Porous Sampling Nib with Multilayer Polyelectrolyte Coating Sintered porous sampling nibs from example 24 were further treated with polyelectrolyte solution to improve hydrophilic stability. The freshly plasma treated sample nibs were immersed in 0.25% polyethylenimine (750 KDa) water-alcohol solution (80% deionized water and 20% isopropyl alcohol) at room temperature for 10 minutes and dried at 50° F. for 10 minutes in an oven and then immersed in 0.25% polyacrylic acid (250 KDa) water-alcohol solution (80% deionized water and 20% isopropyl alcohol) at room temperature for 10 minutes and dried at 50° F. for 10 minutes. The nibs were hydrophilic and adsorbed 20 µl deionized water in less than 3 seconds when 20 µl deionized water was placed on the tip of a nib with a pipette.

EXAMPLE 31

Hydrophilic Sintered Porous Sampling Nib with Polyelectrolyte and Surfactant Coating Sintered porous sampling nibs from example 24 were further treated with a polyelectrolyte solution to improve hydrophilic stability. The freshly plasma treated sample nibs were immersed in 0.25% polyethylenimine (750 KDa) water-alcohol solution (80% deionized water and 20% isopropyl alcohol) at room temperature for 10 minutes and dried at 50° F. for 10 minutes in an oven and then immersed in 0.1% Zonyl® FSK water-alcohol solution (80% deionized water and 20% isopropyl alcohol) at room temperature for 10 minutes and dried at 50° F. for 10 minutes. The nibs were hydrophilic and adsorbed 20 µl deionized water in less than 3 seconds when 20 µl deionized water was placed on the tip of the nib with a pipette.

EXAMPLE 32

Hydrophilic Sintered Porous Sampling Nib with Heparin

Sintered porous sampling nibs from examples 20-23 are treated with surfactant and heparin. The sample nibs are immersed in a water-isopropyl alcohol solution (80:20) comprising 1% Tween® 20 and 0.5% heparin sodium salt at room temperature for 12 hours and dried at 70° F. for 8 hours in an oven. The nibs become hydrophilic and adsorb 20 µl deionized water in less than 3 seconds when 20 µl deionized water is placed on the tip of a nib with a pipette.

EXAMPLE 33

Hydrophilic Sintered Porous Sampling Nib with Polyelectrolyte and Heparin Coating Sintered porous sampling nibs from example 24 are further treated with polyelectrolyte solution and heparin solution to improve blood compatibility. The freshly plasma treated sample nibs are immersed in 0.25% polyethylenimine (750 KDa) in a water-alcohol solution (80% deionized water:20% isopropyl alcohol) at room temperature for 10 minutes, dried at 50° F. for 10 minutes in an oven and then immersed in a 0.1% heparin sodium salt water solution at room temperature for 10 minutes and dried at 50° F. for 10 minutes The nibs are hydrophilic and adsorb 20 µl deionized water in less than 3 seconds when 20 µl deionized water is placed on the tip of a nib with a pipette.

EXAMPLE 34

Sintered Hydrophilic Porous Sampling Nib Comprising C-18 Silica Gel

A powdered mixture comprising 70% of UHMWPE polyethylene having an average particle size of about 30 µm and 30% of C-18 silica gel with average particle size of 30 µm is filled into the cavities of an aluminum mold, heated to 350° F. for about three minutes and subsequently cooled to room temperature in about five minutes. The sintered porous composite nib has an average pore size of about 10 µm and porous volume of about 40%. The nibs can be further treated with surfactant solution to provide hydrophilicity.

EXAMPLE 35

Sintered Hydrophilic Porous Sampling Nib Comprising Ion Exchange Resins

A powdered mixture comprising 70% of UHMWPE polyethylene having an average particle size of about 30 µm and 30% of Dowex® 50WX2 fine mesh resin (200 to 400 meshes) with average particle size of 50 µm is filled into the cavities of an aluminum mold, heated to 350° F. for about three minutes and subsequently cooled to room temperature in about five minutes. The sintered porous composite nib has an average pore size of about 12 µm and porous volume of about 40%. The nibs can be further treated with surfactant solution to provide hydrophilicity.

EXAMPLE 36

Sintered Hydrophilic Porous Sampling Nib Comprising Chelating Agents

A powdered mixture comprising 95% of UHMWPE polyethylene having an average particle size of about 30 µm and 5% of ethylenediaminetetraacetic acid (EDTA) powder with average particle size of 50 µm is filled into the cavities of an aluminum mold, heated to 350° F. for about three minutes and subsequently cooled to room temperature in about five minutes. The sintered porous composite nib has an average pore size of about 10 µm and porous volume of about 40%. The nibs can be further treated with surfactant solution to provide hydrophilicity.

EXAMPLE 37

Sintered Hydrophilic Porous Sampling Nib Comprising DNA Stabilizing Agents

A powdered mixture comprising 98% of UHMWPE polyethylene having an average particle size of about 30 µm and 2% of uric acid powder with average particle size of 50 µm is filled into the cavities of an aluminum mold, heated to 350° F. for about three minutes and subsequently cooled to room temperature in about five minutes. The sintered porous composite nib has an average pore size of about 10 µm and porous volume of about 40%. The nibs can be further treated with surfactant solution to provide hydrophilicity.

EXAMPLE 38

Sintered Hydrophilic Porous Sampling Nib Comprising Chaotropic Agents

A powdered mixture comprising 98% of UHMWPE polyethylene having an average particle size of about 30 µm and 2% of guanidinium chloride powder with average particle size of 50 µm is filled into the cavities of an aluminum mold, heated to 350° F. for about three minutes and subsequently cooled to room temperature in about five minutes. The sintered porous composite nib has an average pore size of about 10 µm and porous volume of about 40%. The nibs can be further treated with surfactant solution to provide hydrophilicity.

EXAMPLE 39

Sintered Hydrophilic Porous Sampling Nib Comprising Multiple Additives for Blood Preservation A powdered mixture comprising 90% of UHMWPE polyethylene having an average particle size of about 30 µm, 2% of uric acid powder with average particle size of 50 µm, 2% of guanidinium chloride powder with average particle size of 50 µm, 5% of ethylenediaminetetraacetic acid (EDTA) powder with average particle size of 50 µm and 1% of sodium dodecyl sulfate (SDS) powder is filled into the cavities of an aluminum mold, heated to 350° F. for about three minutes and subsequently cooled to room temperature in about five minutes. The sintered porous composite nib has an average pore size of about 12 µm and porous volume of about 40%. The nibs are hydrophilic and adsorb 20 µl deionized water in less than 3 seconds when 20 µl deionized water is placed on the tip of a nib with a pipette.

EXAMPLE 40

Recovery of Caffeine from Sintered Hydrophilic Nib

A Porex hydrophilic sintered polyethylene pen nib with an average pore size of 40 microns and pore volume of 38% was selected for test sampling properties. Artificial plasma was formulated with phosphate buffer, red food dye, bovine serum albumin and sodium azide. Different volumes (10 µl, 20 µl, 40 µl, and 100 µl of the artificial plasma were absorbed into different porous nibs. These different nibs had clearly visible differences in the amount of sample as indicated by the extent of the dye.

Figure 18:
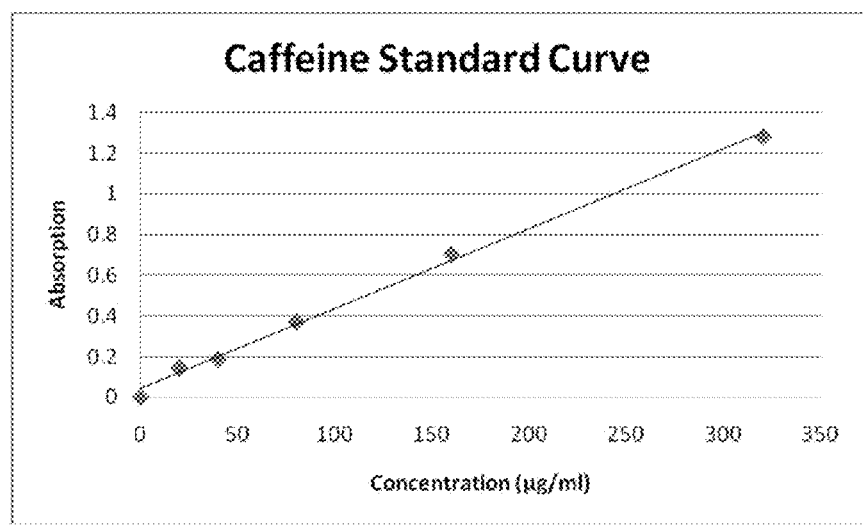
FIG. 18. Standard curve of UV Absorption for serial dilution of caffeine in water.

Caffeine was obtained from Sigma Aldrich. Caffeine was mixed with artificial plasma to form a 10 mg/ml solution. A caffeine standard solution (10 mg caffeine/ml) was made and serially diluted in deionized water solution. The standard UV absorption curve for these serially diluted caffeine solutions is shown in FIG. 18. The UV absorption was measured on a Thermo-Fisher NanoDrop 2000 machine. The caffeine was measured at the wavelength of 273 nm. The wavelength selection was based on the caffeine UV absorption curve and the UV absorption curve for artificial plasma.

20 µl of artificial plasma containing 10 mg/ml caffeine (total of 200 µg caffeine) was adsorbed into a Porex nib. The nib was dried at room temperature open to air for 2 hours. The Porex nib was cut with a blade to remove the sample containing caffeine, as indicated by the dye. The samples of the cut nib containing the caffeine sample was separately transferred into a 7 ml glass vial. The sample in the vial was extracted with 1 ml deionized water for 2 hours.

The UV absorption of this aqueous extract was measured for the sample with artificial plasma and the sample with caffeine in the artificial plasma. The difference for the same sample with and without caffeine was measured for caffeine released from the nib sample. The readings were estimated to the closest 5 µg/ml using the caffeine deionized water standard curve. The results in Table 1 show a caffeine recovery of 77% from the nib.

TABLE 1

| Caffeine recovery for Porex nib | | | | |
|---|---|---|---|---|
| Sample | UV Absorption (273 nm) | Factor (size) | Measured Caffeine Concentration (µg) | Recovery % |
| Porex nib | 0.70 | 1 | 155 | 77 |

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A device for liquid sample collection comprising:
 a porous nib comprising a nib tip and a nib stem, the nib tip comprising a hydrophilic sintered porous polymer and the nib stem comprising a different material, the nib tip configured to collect a liquid sample, and the nib stem configured to secure the porous nib in a housing; and,
 the housing comprising a first end configured to receive and support the nib stem of the porous nib and a second closeable end, wherein the housing further comprises a system for advancing and retracting the porous nib through the first end of the housing.

2. The device of claim 1, wherein the nib stem comprises a hydrophobic nib stem.

3. The device of claim 1, further comprising a cap.

4. The device of claim 1, wherein the porous nib comprises plastic, metal, glass, or ceramic.

5. The device of claim 4, wherein the porous plastic nib comprises polyethylene, polypropylene, polyvinylidene fluoride, polyamide, polyacrylate, polyacrylic nitrile, ethylene-vinyl acetate, polyester, polycarbonate, polystyrene, polytetrafluoroethylene, or cellulose, or a combination thereof.

6. The device of claim 5, wherein the porous plastic nib comprises polyethylene and the polyethylene is high density polyethylene, low density polyethylene, or ultra high molecular weight polyethylene, or a combination thereof.

7. The device of claim 1, wherein the device is in a shape of a pen.

8. The device of claim 1, wherein the porous nib tip comprises one or more preset markers that allow the porous nib tip to break into segments.

9. The device of claim 1, wherein the housing further comprises a reservoir.

10. The device of claim 1, wherein the device may be connected to a mass spectrometer so that the porous nib is in proximity to a sample receiving chamber in the mass spectrometer.

11. The device of claim 1, wherein the device stores a sample, transports a sample, or delivers a sample to a receptacle.

12. The device of claim 1, wherein the nib tip comprises sintered porous plastic.

13. The device of claim 1, wherein the porous nib further comprises a functional additive.

14. The device of claim 1, wherein the housing is electrically conductive.

15. A method of making the device of claim 1, comprising:
 (a) forming the porous nib of claim 1; and,
 (b) securing the porous nib to a pen-like housing.

16. The method of making the device of claim 15, wherein (a) forming a porous nib comprises forming a porous nib having a nib tip and a nib stem; and wherein (b) securing the porous nib to a pen-like housing comprises inserting the nib stem into an opening of the pen-like housing.

17. A method of using the device of claim 1, comprising
 (a) contacting the porous nib with a liquid sample to be collected; and,
 (b) allowing the liquid sample to be absorbed into the porous nib.

18. The method of claim 17, further comprising allowing the sample to dry on the porous nib.

19. The method of claim 17, further comprising capping the nib, retracting the nib into the device, or both.

20. The method of claim 18, further comprising
 (a) releasing the porous nib into a container;
 (b) extracting an analyte from the nib with a solvent or a solution; and,
 (c) detecting the analyte in the extracted solution.

21. The method of claim 20, wherein the detecting the analyte in the extracted solution is conducted using a mass spectrometer.

22. The method of claim 18, further comprising:
 (a) wetting the porous nib containing the dried sample with a solution;
 (b) applying an electrical potential to the wet porous nib; and,
 (c) detecting ionized analytes released from the wet porous nib using a mass spectrometer.

23. The method of claim 18, further comprising:
 (a) wetting the porous nib containing the dried sample with a solution; and
 (b) applying the wet porous nib to a surface to transfer sample from the wet porous nib to the surface;
 (c) introducing the surface into a mass spectrometer; and,
 (d) detecting ionized analytes released from the nib using the mass spectrometer.

24. The device of claim 1, further comprising a lancet for punching the skin.

25. A method of using the device of claim 24, comprising:
 (a) piercing skin of an animal with the lancet to release blood;
 (b) contacting the blood with the porous nib;
 (c) allowing the blood to be absorbed into the porous nib;
 (d) allowing the blood to dry on the porous nib; and,
 (e) capping the porous nib in the device housing.

* * * * *